United States Patent
Shimada et al.

(10) Patent No.: US 6,545,000 B1
(45) Date of Patent: Apr. 8, 2003

(54) [1,2,4]TRIAZOLO[1,5-C]PYRIMIDINE DERIVATIVES

(75) Inventors: Junichi Shimada, Shizuoka (JP); Hironori Imma, Shizuoka (JP); Naoto Osakada, Shizuoka (JP); Shizuo Shiozaki, Shizuoka (JP); Tomoyuki Kanda, Shizuoka (JP); Yoshihisa Kuwana, Shizuoka (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/787,779

(22) PCT Filed: Sep. 22, 1999

(86) PCT No.: PCT/JP99/05176

§ 371 (c)(1),
(2), (4) Date: Mar. 22, 2001

(87) PCT Pub. No.: WO00/17201

PCT Pub. Date: Mar. 30, 2000

(30) Foreign Application Priority Data

Sep. 22, 1998 (JP) ............................................. 10-267178

(51) Int. Cl.$^7$ ..................... C07D 487/04; A61K 31/519; A61P 25/24; A61P 25/28
(52) U.S. Cl. .................. 514/259.31; 544/263; 514/218; 540/480; 540/574
(58) Field of Search ........................... 544/263; 514/258, 514/259.31

(56) References Cited

U.S. PATENT DOCUMENTS

| | | | |
|---|---|---|---|
| 4,477,450 A | 10/1984 | Wade | 424/246 |
| 4,483,987 A | 11/1984 | Wagner | 544/263 |
| 4,572,910 A | 2/1986 | Wade | 514/222 |
| 5,270,311 A | 12/1993 | Caulkett et al. | 514/245 |
| 5,356,894 A | 10/1994 | Rodney et al. | 514/233.2 |

FOREIGN PATENT DOCUMENTS

| | | |
|---|---|---|
| EP | 0 132 851 | 2/1985 |
| EP | 459 702 | 12/1991 |
| EP | 667 349 | 8/1995 |
| EP | 0 976 753 | 2/2000 |
| WO | WO 98/42711 | 10/1998 |

OTHER PUBLICATIONS

Feoktistov et al. TIPS 19: 148–152, 1998.*
European Journal of Pharmacology, Durcan, et al., "Evidence of adenosine $A_2$ receptor in the hypomobility . . .", vol. 168 (1989), pp. 285–290.

* cited by examiner

*Primary Examiner*—Venkataraman Balasubramanian
(74) *Attorney, Agent, or Firm*—Fitzpatrick, Cella, Harper & Scinto

(57) ABSTRACT

The present invention relates to [1,2,4]triazolo[1,5-c] pyrimidine compounds represented by formula (I):

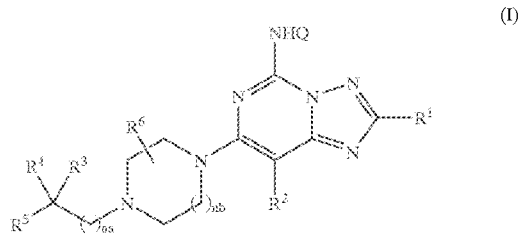

wherein na and nb independently represent an integer of 0 to 4 and Q represents a hydrogen atom or 3,4-dimethoxybenzyl, or salts thereof exhibit activity as adenosine $A_{2A}$ receptor antagonists.

17 Claims, No Drawings

[1,2,4]TRIAZOLO[1,5-C]PYRIMIDINE DERIVATIVES

TECHNICAL FIELD

The present invention relates to [1,2,4]triazolo[1,5-c]pyrimidine derivatives which show adenosine $A_{2A}$ receptor antagonism and are useful for treating or preventing various diseases induced by hyperactivity of adenosine $A_{2A}$ receptors (for example, Parkinson's disease, senile dementia, or depression).

BACKGROUND ART

It is known that adenosine shows attenuation of the activity of neurotransmitters via an $A_{2A}$ receptor (*European Journal of Pharmacology*, 168: 285 (1989)). Consequently, adenosine $A_{2A}$ receptor antagonists are expected as remedies or preventives for various diseases induced by hyperactivity of adenosine $A_{2A}$ receptors, such as a remedy for Parkinson's disease, an anti-dementia drug, a remedy for depression, and the like. Furthermore, the above antagonists are expected to exhibit therapeutic and symptom-improving effects upon Alzheimer's disease, progressive supranuclear palsy, AIDS encephalopathy, propagative spongiform encephalopathy, multiple sclerosis, amyotrophic lateral sclerosis, Huntington's disease, multiple system atrophy, cerebral ischemia, attention deficit hyperactivity disorder, somnipathy, ischemic heart disease, intermittent claudication, diabetes, or the like.

On the other hand, [1,2,4]triazolo[1,5-c]pyrimidine derivatives are disclosed as compounds having diuretic activity in Japanese Published Unexamined Patent Application No. 13792/85, as compounds having antiasthmatic activity in Japanese Published Unexamined Patent Application No. 56983/85, and as compounds having bronchodilative activity in Japanese Published Unexamined Patent Application No. 167592/84.

However, adenosine receptor antagonism of [1,2,4]triazolo[1,5-c]pyrimidine derivatives and their activity on the central nervous system are not known.

DISCLOSURE OF THE INVENTION

An object of the present invention is to provide [1,2,4]triazolo[1,5-c]pyrimidine derivatives or pharmaceutically acceptable salts thereof which have adenosine $A_{2A}$ receptor antagonism and are useful for treating or preventing various diseases induced by hyperactivity of an adenosine $A_{2A}$ receptor (for example, Parkinson's disease, dementia, depression, or the like).

The present invention relates to a [1,2,4]triazolo[1,5-c]pyrimidine derivative represented by formula (I):

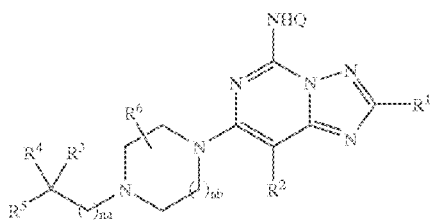

wherein $R^1$ represents substituted or unsubstituted aryl, or a substituted or unsubstituted aromatic heterocyclic group; $R^2$ represents a hydrogen atom, halogen, substituted or unsubstituted lower alkyl, substituted or unsubstituted aryl, or a substituted or unsubstituted aromatic heterocyclic group; na and nb are the same or different, and each represents an integer of 0 to 4; Q represents a hydrogen atom or 3,4-dimethoxybenzyl; $R^6$ represents a hydrogen atom, substituted or unsubstituted lower alkyl, halogen, or hydroxy; $R^3$ represents (i) hydroxy, (ii) hydroxy-lower alkyl, (iii) substituted or unsubstituted lower alkoxy, or (iv) a group selected from the group consisting of substituted or unsubstituted imidazo[1,2-a]pyridyl, substituted or unsubstituted imidazo[1,2-a]pyrazinyl, substituted or unsubstituted imidazo[1,2-a]pyrimidinyl, substituted or unsubstituted benzimidazolyl, substituted or unsubstituted benzothiazolyl, substituted or unsubstituted benzo-2,1,3-thiadiazolyl, substituted or unsubstituted isoxazolyl, and substituted or unsubstituted 3-oxo-3,4-dihydro-2H-benzo[1,4]oxazinyl; and when $R^3$ represents hydroxy, hydroxy-lower alkyl, or substituted or unsubstituted lower alkoxy, $R^4$ and $R^5$ are the same or different, and each represents a substituted or unsubstituted lower alkyl or substituted or unsubstituted aryl, or $R^4$ and $R^5$ form a substituted or unsubstituted saturated carbocycle together with the adjacent carbon atom, and when $R^3$ represents a group selected from the group consisting of substituted or unsubstituted imidazo[1,2-a]pyridyl, substituted or unsubstituted imidazo[1,2-a]pyrazinyl, substituted or unsubstituted imidazo[1,2-a]pyrimidinyl, substituted or unsubstituted benzimidazolyl, substituted or unsubstituted benzothiazolyl, substituted or unsubstituted benzo-2,1,3-thiadiazolyl, substituted or unsubstituted isoxazolyl, and substituted or unsubstituted 3-oxo-3,4-dihydro-2H-benzo[1,4]oxazinyl, $R^4$ and $R^5$ are the same or different, and each represents a hydrogen atom, substituted or unsubstituted lower alkyl, or substituted or unsubstituted aryl, or $R^4$ and $R^5$ form a substituted or unsubstituted saturated carbocycle together with the adjacent carbon atom; or a pharmaceutically acceptable salt thereof.

In other aspect, the present invention relates to a medicament comprising the [1,2,4]triazolo[1,5-c]pyrimidine derivative represented by formula (I) or a pharmaceutically acceptable salt thereof.

In still other aspect, the present invention relates to an adenosine $A_{2A}$ receptor antagonist or an agent for preventing or treating a disease induced by hyperactivity of an adenosine $A_{2A}$ receptor, comprising the [1,2,4]triazolo[1,5-c]pyrimidine derivative represented by formula (I) or a pharmaceutically acceptable salt thereof, In still other aspect, the present invention relates to use of the [1,2,4]triazolo[1,5-c]pyrimidine derivative represented by formula (I) or a pharmaceutically acceptable salt thereof for the preparation of an agent for preventing or treating a disease induced by hyperactivity of an adenosine $A_{2A}$ receptors.

In further aspect, the present invention relates to a method for preventing or treating a disease induced by hyperactivity of an adenosine $A_{2A}$ receptor, comprising administering an effective amount of the [1,2,4]triazolo[1,5-c]pyrimidine derivative represented by formula (I) or a pharmaceutically acceptable salt thereof.

In the definition of each group in formula (I), examples of the alkyl moiety of the lower alkyl, lower alkoxy, and hydroxy-lower alkyl include linear or branched alkyl groups having 1 to 6 carbon atoms, such as methyl, ethyl, propyl, isopropyl, butyl, isobutyl, sec-butyl, tert-butyl, pentyl, neopentyl, hexyl, and the like. Examples of the halogen include fluorine, chlorine, bromine and iodine atoms. Examples of the aryl include phenyl, naphthyl, indenyl, anthryl, and the like. Examples of the aromatic heterocyclic group include furyl, thienyl, pyrrolyl, pyridyl, oxazolyl, thiazolyl, imidazolyl, pyrimidinyl, triazinyl, indolyl, quinolyl, purinyl, benzoxazolyl, benzothiazolyl, benzimidazolyl, and the like. Examples of the saturated carbocycle include those having 3 to 8 carbon atoms, such as cyclopropane, cyclobutane, cyclopentane, cyclohexyane cycloheptane, cyclooctane, and the like.

Examples of the substituent in the substituted lower alkyl, substituted lower alkoxy, and substituted saturated carbocycle include 1 to 3 substituents which are the same or different, such as hydroxy, carboxy, a saturated carbocyclic group, lower alkoxy, lower alkoxycarbonyl, aryl, aryloxy, aralkyloxy, an aromatic heterocyclic group, a lower alkyl-substituted aromatic heterocyclic group, hydroxy-substituted lower alkoxy, lower alkoxy-substituted lower alkoxy, lower alkanoyl, aryl-substituted lower alkanoyl, aroyl, formyl, halogen, trifluoromethyl, vinyl, styryl, phenylethynyl, and the like. The saturated carbocyclic group means a group formed by removing one hydrogen atom from the above-described saturated carbocycle. The lower alkyl moiety of the lower alkoxy, lower alkoxycarbonyl, lower alkyl-substituted aromatic heterocyclic group, hydroxy-substituted lower alkoxy, lower alkoxy-substituted lower alkoxy, lower alkanoyl, and aryl-substituted lower alkanoyl has the same meaning as the above-described lower alkyl. The aryl and the aryl moiety of the aryloxy, aralkyloxy, aryl-substituted lower alkanoyl, and aroyl have the same meanings as the above-described aryl. The aromatic heterocyclic group and the aromatic heterocyclic moiety of the lower alkyl-substituted aromatic heterocyclic group have the same meanings as the above-described aromatic heterocyclic group. The alkylene moiety of the aralkyloxy means a group formed by removing one hydrogen atom from the above-described lower alkyl. The halogen has the same meaning as the above-described halogen.

Examples of the substituent of the substituted aryl, substituted aromatic heterocyclic group, and group selected from the group consisting of substituted imidazo[1,2-a]pyridyl, substituted imidazo[1,2-a]pyrazinyl, substituted imidazo[1,2-a]pyrimidinyl, substituted benzimidazolyl, substituted benzothiazolyl, substituted benzo-2,1,3-thiadiazolyl, substituted isoxazolyl, and substituted 3-oxo-3,4-dihydro-2H-benzo[1,4]oxazinyl include 1 to 3 substituents which are the same or different, such as lower alkyl, hydroxy, hydroxy-substituted lower alkyl, halogeno-lower alkyl, lower alkoxy, lower alkoxycarbonyl, lower alkylthio, lower alkylsulfinyl, lower alkylsulfonyl, aryl, aryloxy, aralkyl, aralkyloxy, an aromatic heterocyclic group, halogenoaryloxy, halogenoaralkyloxy, carboxy, carbamoyl, formyl, lower alkanoyl, aroyl, halogen, nitro, amino, cyano, trifluoromethyl, trifluoromethoxy, methylenedioxy, ethylenedioxy, and the like. The lower alkyl and the lower alkyl moiety of the hydroxy-substituted lower alkyl, halogeno-lower alkyl, lower alkoxy, lower alkoxycarbonyl, lower alkylthio, lower alkylsulfinyl, lower alkylsulfonyl, and lower alkanoyl have the same meanings as the above-described lower alkyl. The aryl and the aryl moiety of the aryloxy, halogenoaryloxy, and aroyl have the same meanings as the above-described aryl. The aryl moiety of the aralkyl, aralkyloxy, and halogenoaralkyloxy has the same meaning as the above-described aryl. The alkylene moiety of the aralkyl, aralkyloxy, and halogenoaralkyloxy means a group formed by removing one hydrogen atom from the above-described lower alkyl. The halogen and the halogen moiety of the halogeno-lower alkyl, halogenoaryloxy, and halogenoaralkyloxy have the same meanings as the above-described halogen. The aromatic heterocyclic group has the same meaning as described above.

Hereinafter, the compound represented by formula (I) is referred to as Compound (I). Compounds of other formula numbers are also called similarly. Among Compounds (I), a compound, wherein Q is 3,4-dimethoxybenzyl, is hereinafter referred to Compound (IQ) which has excellent adenosine $A_{2A}$ receptor antagonism and is also useful as a synthetic intermediate for a compound, wherein Q is a hydrogen atom, among Compounds (I). A compound, wherein Q is a hydrogen atom in formula (I) is referred to as Compound (IH), if necessary.

Preferred examples in the present invention include Compounds (IH), wherein Q is a hydrogen atom in formula (I). Preferred examples of Compound (IH) are shown below. Preferred are compounds, wherein $R^2$ is a hydrogen atom, more preferred are compounds, wherein $R^2$ is a hydrogen atom; and $R^1$ is a substituted or unsubstituted aromatic heterocyclic group, and particularly preferred are compounds, wherein nb is 1. Also, compounds, wherein $R^1$ is furyl; and $R^2$ is a hydrogen atom, compounds, wherein $R^1$ is furyl; $R^2$ and $R^6$ each are a hydrogen atom; na and nb each are 1; $R^3$ is hydroxy; and $R^4$ and $R^5$ each are a substituted or unsubstituted lower alkyl (particularly, methyl is preferred), and compounds, wherein $R^1$ is furyl; $R^2$, $R^4$, $R^5$ and $R^6$ each are a hydrogen atom; na is 0; nb is 1; and $R^3$ is a group selected from the group consisting of substituted or unsubstituted imidazo[1,2-a]pyridyl, substituted or unsubstituted imidazo[1,2-a]pyrazinyl, substituted or unsubstituted imidazo[1,2-a]pyrimidinyl, substituted or unsubstituted benzimidazolyl, substituted or unsubstituted benzothiazolyl, substituted or unsubstituted benzo-2,1,3-thiadiazolyl, substituted or unsubstituted isoxazolyl, and substituted or unsubstituted 3-oxo-3,4-dihydro-2H-benzo[1,4]oxazinyl (particularly, 5-methylisoxazol-3yl is preferred) are preferred compounds.

Examples of the pharmaceutically acceptable salts of Compound (I) include pharmaceutically acceptable metal salts, ammonium salts, organic amine addition salts, amino acid addition salts, acid addition salts, and the like. The pharmaceutically acceptable metal salts of Compound (I) include alkali metal salts, such as sodium salts, potassium salts and the like, alkaline earth metal salts, such as magnesium salts, calcium salts and the like, aluminum salts, zinc salts and the like. The pharmaceutically acceptable ammonium salts include salts such as ammonium, tetramethylammonium and the like. The pharmaceutically acceptable organic amine addition salts include addition salts of morpholine, piperidine and the like. The pharmaceutically acceptable amino acid addition salts include addition salts of lysine, glycine, phenylalanine, and the like. The pharmaceutically acceptable acid addition salts include inorganic acid salts, such as hydrochlorides, sulfates, phosphates, and the like, and organic acid salts, such as acetates, maleates, fumarates, tartrates, citrates, and the like.

The production methods of Compounds (I) are explained below.

Production Method 1

Compound (IH) can be produced via Compound (IQ) by the following reaction steps.

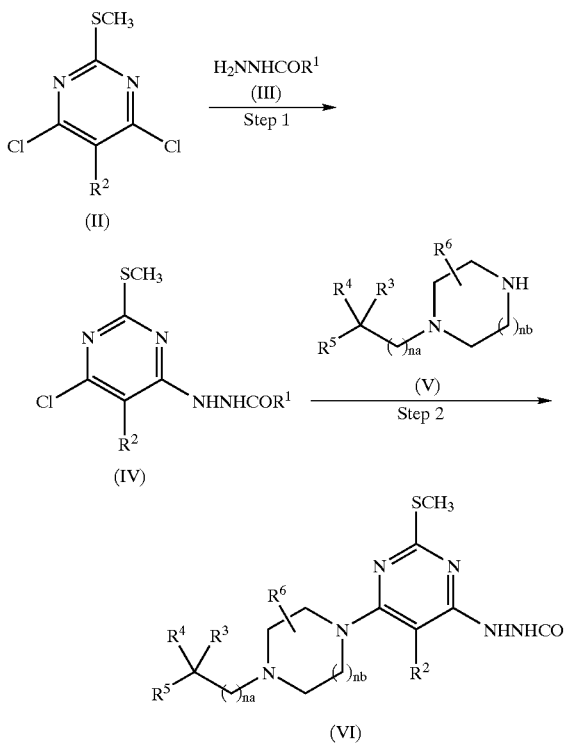

(wherein $R^1$, $R^2$, $R^3$, $R^4$, $R^5$, $R^6$, na and nb have the same meanings as defined above, respectively)

Step 1

Starting Compound (II) is commercially available (manufactured by Aldrich) or can be synthesized in accordance with a known method (*Journal of Chemical Society*, 383 (1943)) or a method similar thereto. Also, Compound (III) is commercially available (manufactured by Aldrich, etc.) or can be synthesized in accordance with a known method (*New Experimental Chemistry Course*, 14, Syntheses and Reactions of Organic Compounds (II), p. 1221 (1977) (Maruzen)) or a method similar thereto.

Compound (IV) can be obtained by reacting Compound (II) with 1 to 5 equivalents, preferably 1 to 2 equivalents, of Compound (III) in a solvent inert to the reaction in the presence of 1 to 3 equivalents, preferably 2 equivalents, of a suitable base, generally at room temperature to 200° C., preferably at room temperature, for 10 minutes to 48 hours. Examples of the solvent inert to the reaction include tetrahydrofuran (hereinafter referred to as "THF"), dioxane, diethylene glycol, N,N-dimethylformamide (hereinafter referred to as "DMF"), dimethylacetamide, dimethyl sulfoxide (hereinafter referred to as "DMSO"), benzene, toluene, xylene, acetonitrile, ethyl acetate, pyridine, tetralin, methylene chloride, chloroform, methanol, ethanol, propanol, butanol, and the like, which can be used alone or in combination, and preferred example are THF and DMF. Examples of the suitable base include triethylamine, diisopropylethylamine, 1,8-diazabicyclo[5.4.0]-7-undecene (hereinafter referred to as "DBU"), pyridine, N-methylmorpholine, potassium carbonate, sodium hydride, calcium hydride, and the like, and a preferred example is DBU.

Step 2

Starting Compound (V) is commercially available or can be synthesized in accordance with a known method (*J. Org. Chem.*, 8: 338 (1943); Japanese Published Unexamined Patent Application No. 106375/99) or a method similar thereto.

Compound (VI) can be obtained by reacting Compound (IV) with one equivalent to a large excess of Compound (V) without a solvent or in a solvent inert to the reaction in the presence of 0.1 to 3 equivalents, preferably 1.2 equivalents, of a suitable base, generally at room temperature to 200° C., preferably at 100 to 150° C., for 10 minutes to 48 hours. Examples of the solvent inert to the reaction include THF, dioxane, diethylene glycol, DMF, dimethylacetamide, DMSO, benzene, toluene, xylene, acetonitrile, ethyl acetate, pyridine, tetralin, methylene chloride, chloroform, and the like, which can be used alone or in combination, and preferred examples are DMF and THF. Examples of the suitable base include triethylamine, diisopropylethylamine, DBU, pyridine, N-methylmorpholine, potassium carbonate, sodium hydride, calcium hydride, and the like, and preferred example are DBU and potassium carbonate.

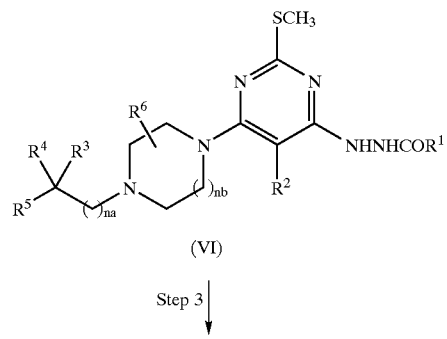

(VI)

Step 3

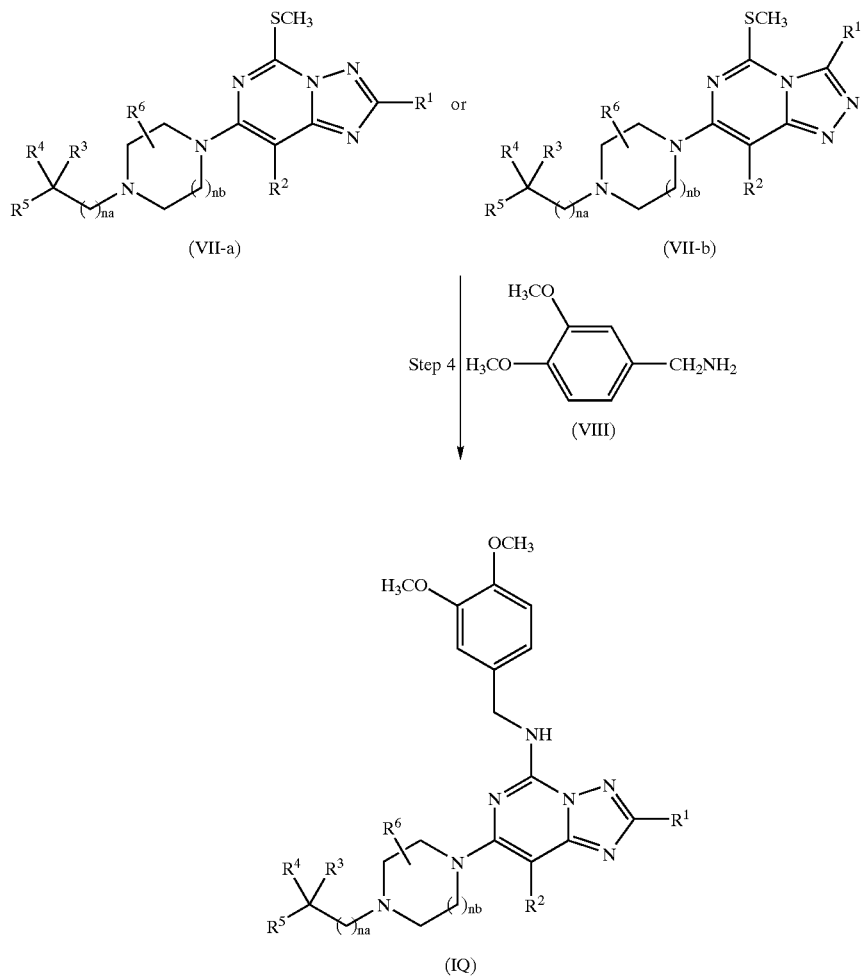

(wherein $R^1$, $R^2$, $R^3$, $R^4$, $R^5$, $R^6$, na and nb have the same meanings as defined above, respectively)

Step 3

Compound (VII-a) or Compound (VII-b) can be obtained by treating Compound (VI) with 2 to 10 equivalents of a dehydrating-condensing agent, such as polyphosphoric acid, ethyl polyphosphate, trimethylsilyl polyphosphate, or the like, without a solvent or in a solvent inert to the reaction, generally at 10 to 200° C., preferably at 130 to 150° C., for 1 to 24 hours, preferably for 4 to 7 hours. The reaction for production of Compound (VII-a) in this step is known as Dimroth rearrangement reaction (for example, see *Journal of Medicinal Chemistry*, 33: 1231 (1990)). Examples of the solvent inert to the reaction include benzene, toluene, xylene, tetralin, phenyl ether, methylene chloride, chloroform, and the like, which are used alone or in combination, and a preferred example is xylene.

Step 4

Compound (IQ) can be obtained by reacting Compound (VII-a) or Compound (VII-b) with 1 to 6 equivalents, preferably 3 equivalents, of 3,4-dimethoxybenzylamine (VIII) without a solvent or in a solvent inert to the reaction, generally at 10 to 200° C., preferably at 130 to 150° C., for 10 minutes to 24 hours. This step also accompanies the Dimroth rearrangement reaction described in Step 3. Examples of the solvent inert to the reaction include THF, dioxane, diethylene glycol, DMF, dimethylacetamide, DMSO, benzene, toluene, xylene, acetonitrile, ethyl acetate, pyridine, tetralin, methylene chloride, chloroform, methanol, ethanol, propanol, butanol, and the like, which are used alone or in combination, and a preferred example is DMSO.

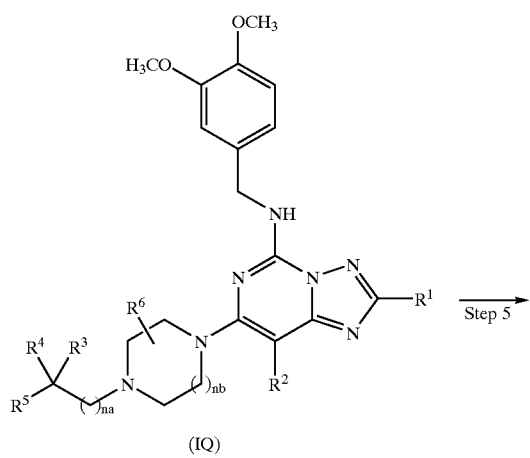

(IQ)

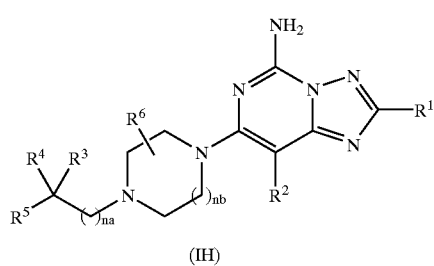

(IH)

(wherein $R^1$, $R^2$, $R^3$, $R^4$, $R^5$, $R^6$, na and nb have the same meanings as defined above, respectively)

Step 5

Compound (IH) can be obtained by treating Compound (IQ) in an acidic solvent, such as hydrochloric acid, acetic acid, dichloroacetic acid, trifluoroacetic acid, trifluoromethanesulfonic acid, or the like, preferably in trifluoroacetic acid or a mixed solvent of trifluoroacetic acid and trifluoromethanesulfonic acid, generally at 10 to 100° C. for 10 minutes to 24 hours, or by treating Compound (IQ) with 1 to 10 equivalents, preferably 5 equivalents, of trifluoromethanesulfonic acid or sulfuric acid in an acidic solvent, such as hydrochloric acid, acetic acid, dichloroacetic acid, trifluoroacetic acid, or the like, preferably in trifluoroacetic acid, in the presence of 1 to 10 equivalents, preferably 4 equivalents, of anisole, dimethoxybenzene or trimethoxybenzene, preferably anisole, generally at –20 to 80° C., preferably at 10 to 40° C., for 10 minutes to 18 hours.

Production Method 2

As an alternative method, Compound (IH) can also be produced by the following steps.

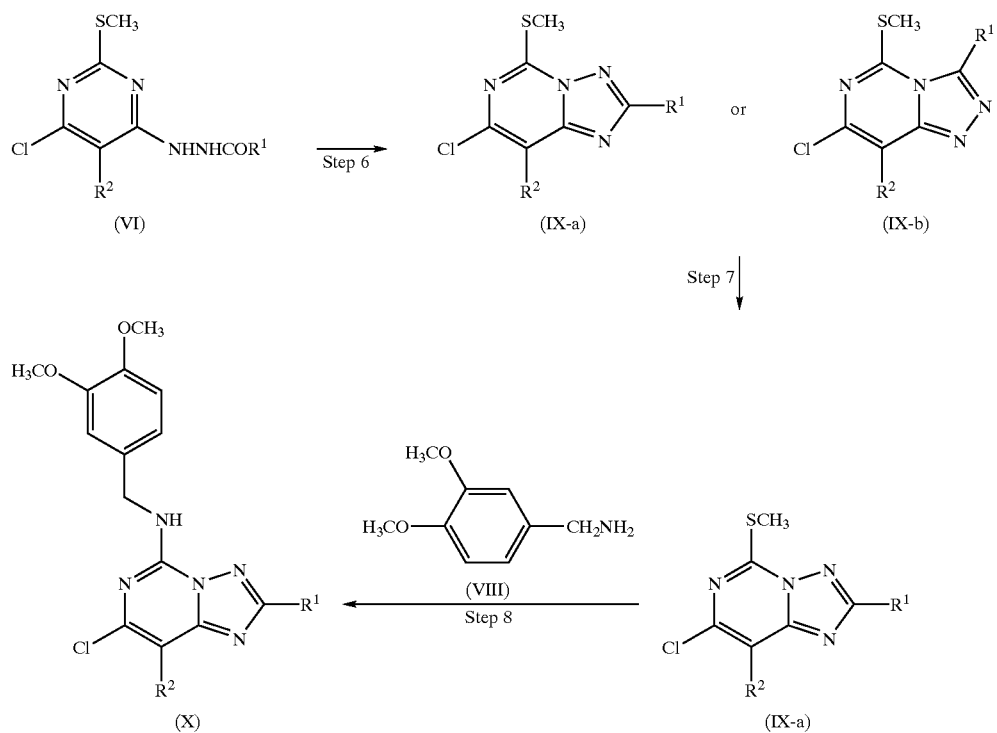

(wherein $R^1$ and $R^2$ have the same meanings as defined above, respectively)

Step 6

Compound (IX-a) or Compound (IX-b) can be obtained by treating Compound (IV) with 2 equivalents to a large excess of a dehydrating-condensing agent, such as polyphosphoric acid, ethyl polyphosphate, trimethylsilyl polyphosphate, or the like, without a solvent or in a solvent inert to the reaction, generally at 10 to 200° C., preferably at 130 to 160° C., for 1 to 12 hours, preferably for 3 to 6 hours. This step also accompanies the Dimroth rearrangement reaction described in Step 3. Examples of the solvent inert to the reaction include toluene, xylene, tetralin, phenyl ether, methylene chloride, chloroform, hexane, and the like, which are used alone or in combination, and a preferred example is xylene.

Step 7

Compound (IX-a) alone can be obtained via the Dimroth rearrangement reaction described in Step 3 by treating a mixture of Compound (IX-a) and Compound (IX-b) or Compound (IX-b) alone in a solvent inert to the reaction in the presence of 0.5 to 3 equivalents, preferably one equivalent, of a suitable base, generally at 0 to 100° C., preferably at 10 to 40° C., for 5 minutes to 10 hours. Examples of the solvent inert to the reaction include THF, dioxane, diethylene glycol, DMF, dimethylacetamide, DMSO, benzene, toluene, xylene, acetonitrile, ethyl acetate, pyridine, tetralin, methylene chloride, chloroform, methanol, ethanol, propanol, butanol, and the like, which are used alone or in combination, and preferred examples are DMF and THF. Examples of the suitable base include triethylamine, diisopropylethylamine, DBU, pyridine, N-methylmorpholine, potassium carbonate, sodium hydride, calcium hydride, and the like, and a preferred example is DBU.

Step 8

Compound (X) can be obtained by reacting Compound (IX-a) with 1 to 6 equivalents, preferably 3 equivalents, of 3,4-dimethoxybenzylamine (VIII) without a solvent or in a solvent inert to the reaction, generally at 0 to 200° C., preferably at 40 to 60° C., for 10 minutes to 24 hours. Examples of the solvent inert to the reaction include THF, dioxane, diethylene glycol, DMF, dimethylacetamide, DMSO, benzene, toluene, xylene, acetonitrile, ethyl acetate, pyridine, tetralin, and the like, which are used alone or in combination, and a preferred example is THF.

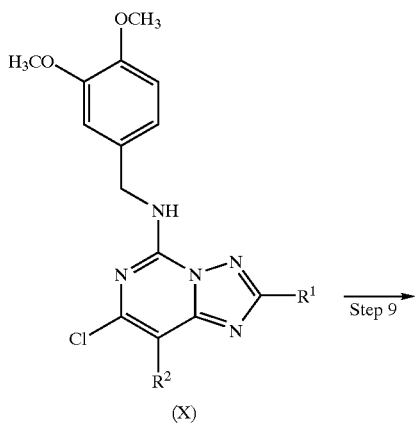

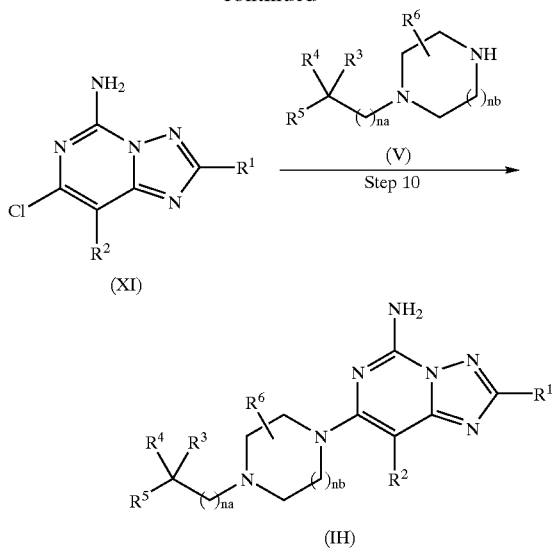

(wherein $R^1$, $R^2$, $R^3$, $R^4$, $R^5$, $R^6$, na and nb have the same meanings as defined above, respectively)

Step 9

Compound (XI) can be obtained by treating Compound (X) for 10 minutes to 24 hours in an acidic solvent, such as hydrochloric acid, acetic acid, dichloroacetic acid, trifluoroacetic acid, trifluoromethanesulfonic acid, or the like, preferably in trifluoroacetic acid or a mixed solvent of trifluoroacetic acid and trifluoromethanesulfonic acid, or by treating Compound (X) with 1 to 10 equivalents, preferably 2.5 equivalents, of trifluoromethanesulfonic acid in an acidic solvent, such as hydrochloric acid, acetic acid, dichloroacetic acid, trifluoroacetic acid, or the like, preferably in trifluoroacetic acid, in the presence of 1 equivalent to a large excess, preferably 3 to 5 equivalents, of anisole, dimethoxybenzene, or trimethoxybenzene, preferably anisole, generally at −20 to 100° C., preferably at 10 to 40° C., for 10 minutes to 18 hours.

Step 10

Compound (IH) can be obtained by reacting Compound (XI) with 1 to 10 equivalents, preferably 3 to 5 equivalents, of Compound (V) without a solvent or in a solvent inert to the reaction, optionally in the presence of 1 to 5 equivalents, preferably 1.5 equivalents, of a suitable base, generally at 10 to 200° C. for 10 minutes to 48 hours. Examples of the solvent inert to the reaction include THF, dioxane, diethylene glycol, ethoxyethanol, DMF, dimethylacetamide, dimethylimidazolidinone (DMI), DMSO, benzene, toluene, xylene, acetonitrile, ethyl acetate, pyridine, tetralin, methylene chloride, chloroform, and the like, which are used alone or in combination, and a preferred example is DMSO. Examples of the suitable base include triethylamine, diisopropylethylamine, DBU, pyridine, N-methylmorpholine, potassium carbonate, sodium carbonate, sodium hydride, calcium hydride, and the like, and preferred examples are potassium carbonate and sodium carbonate.

Production Method 3

As an alternative method, Compound (IH) can also be produced by the following steps.

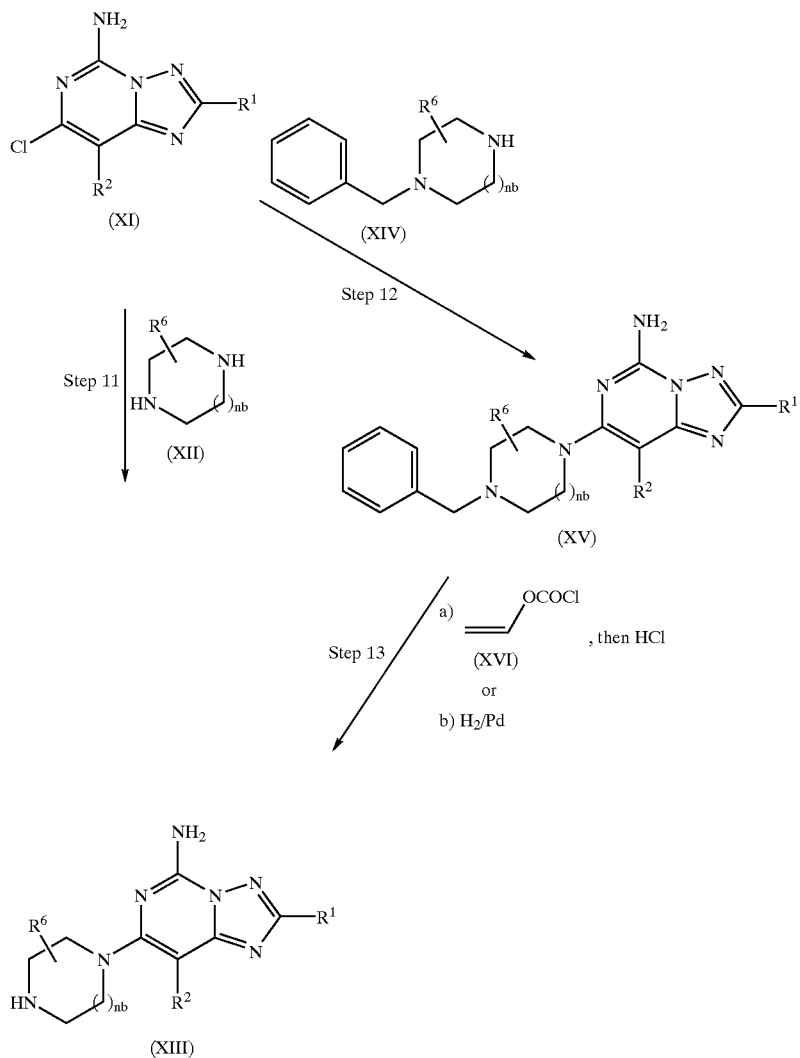

(wherein $R^1$, $R^2$, $R^6$ and nb have the same meanings as defined above, respectively)

Step 11

Compound (XIII) can be obtained by reacting Compound (XI) with Compound (XII) in a similar manner to the method shown in Step 10.

Step 12

Compound (XV) can be obtained by reacting Compound (XI) with Compound (XIV) in a similar manner to the method shown in Step 10.

Step 13

Compound (XIII) can be obtained by reacting Compound (XV) with 1 to 5 equivalents, preferably 1.2 equivalents, of vinyl chlorocarbonate (XVI) in a solvent inert to the reaction, generally at 0 to 100° C., preferably at 10 to 40° C., for 10 minutes to 24 hours, and then treating the reaction product in a solvent inert to the reaction containing 1 to 4 mol/l of hydrogen chloride, generally at 0 to 100° C., preferably at 10 to 40° C., for 10 minutes to 24 hours. Examples of the solvent used in the reaction with vinyl chlorocarbonate (XVI) include dichloromethane, chloroform, carbon tetrachloride, benzene, toluene, THF, DMF, diethyl ether, and the like, which are used alone or in combination, and a preferred example is chloroform. Examples of the solvent used in the treatment with hydrogen chloride include methanol, ethanol, propanol, isopropanol, ethyl acetate, dioxane, and the like, which are used alone or in combination, and a preferred example is methanol. Also, Compound (XIII) can be obtained from Compound (XV) by subjecting it to usual catalytic hydrogenation.

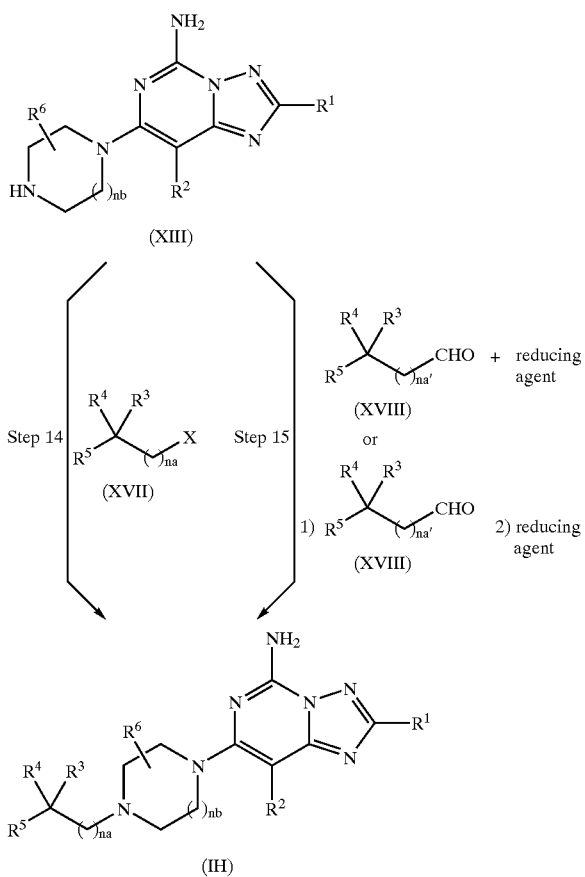

(wherein $R^1$, $R^2$, $R^3$, $R^4$, $R^5$, $R^6$, na and nb have the same meanings as defined above, respectively; na' represents an integer of 0 to 2; and X represents halogen having the same meaning as defined above)

Step 14

Starting Compound (XVII) can be synthesized in accordance with a known method (*J. Chem. Soc., Perkin Trans. I*, 9: 994 (1976)) or a method similar thereto.

Compound (IH) can be obtained by reacting Compound (XIII) with 1 equivalent to a large excess, preferably 1 to 2 equivalents, of Compound (XVII) in a solvent inert to the reaction, optionally in the presence of 1 to 3 equivalents of a suitable base, generally at 0 to 150° C., preferably at 10 to 70° C., for 10 minutes to 48 hours. Examples of the solvent inert to the reaction include pyridine, DMF, dimethylacetamide, THF, dioxane, diethyl ether, dichloromethane, chloroform, carbon tetrachloride, benzene, toluene, xylene, methanol, ethanol, ethyl acetate, hexane, acetonitrile, and the like, which are used alone or in combination, and preferred examples are pyridine and DMF. Examples of the suitable base include triethylamine, diisopropylethylamine, DBU, N-methylmorpholine, potassium carbonate, sodium hydride, and the like, and a preferred example is triethylamine.

Step 15

Starting Compound (XVIII) can be synthesized in accordance with a known method (Japanese Published Unexamined Patent Application No. 109791/86) or a method similar thereto.

Compound (IH) can be obtained by reacting Compound (XIII) with one equivalent to a large excess, preferably 1 to 10 equivalents, of Compound (XVIII) without a solvent or in a solvent inert to the reaction in the presence of one equivalent to a large excess, preferably 1 to 3 equivalents, of a suitable reducing agent, generally at −78 to 100° C., preferably at 0 to 50° C., for 10 minutes to 24 hours. Alternatively, Compound (IH) can be obtained by reacting Compound (XIII) with one equivalent to a large excess, preferably 1 to 10 equivalents, of Compound (XVIII) without a solvent or in a solvent inert to the reaction, generally at −78 to 100° C., preferably at 0 to 50° C., for 10 minutes to 24 hours, followed by treatment in the presence of one equivalent to a large excess, preferably 1 to 3 equivalents, of a suitable reducing agent, generally at −78 to 100° C., preferably at 0 to 50° C., for 10 minutes to 24 hours. Examples of the solvent inert to the reaction include dichloromethane, chloroform, carbon tetrachloride, dichloroethane, benzene, toluene, xylene, ether, tetrahydrofuran, dioxane, dimethylformamide, dimethylacetamide, acetonitrile, hexane, methanol, ethanol, water, and the like, preferably dichloroethane, dichloromethane, and ethanol, which are used alone or in combination. Examples of the suitable reducing agent include sodium borohydride, sodium triacetoxyborohydride, sodium cyanoborohydride, and the like, and a preferred example is sodium triacetoxyborohydride. In this case, a suitable acid can optionally be added in an amount of a catalytic amount to a large excess, preferably 0.5 to 5 equivalents. Examples of the suitable acid include formic acid, acetic acid, trifluoroacetic acid, propionic acid, hydrochloric acid, and the like, and a preferred example is acetic acid.

Production Method 4

Among Compounds (I), Compound (IH-a), wherein Q is a hydrogen atom and $R^5$ is hydroxy, can be produced from Compound (IH-b), wherein Q is a hydrogen atom and $R^5$ is substituted or unsubstituted lower alkoxy, among Compounds (I), by the following step.

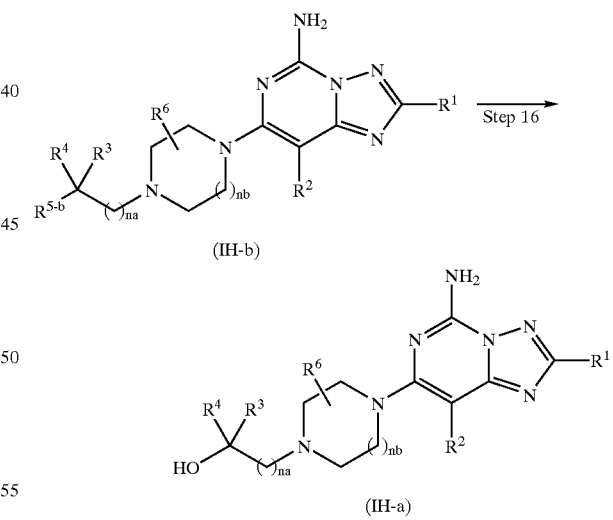

(wherein $R^1$, $R^2$, $R^3$, $R^4$, $R^6$, na and nb have the same meanings as defined above, respectively; and $R^{5-b}$ represents a substituted or unsubstituted lower alkoxy having the same meaning as defined above)

Step 16

Compound (IH-a) can be obtained by treating Compound (IH-b) with one equivalent to a large excess, preferably a large excess, of a suitable sulfur compound without a solvent or in a solvent inert to the reaction in the presence of a catalytic amount to a large excess, preferably 5 to 15 equivalents, of a suitable Lewis acid, generally at −78 to 100° C. for 10 minutes to 72 hours. Examples of the solvent inert to the reaction include dichloromethane, chloroform, carbon tetrachloride, dichloroethane, benzene, toluene, xylene, ether, tetrahydrofuran, dioxane, dimethylformamide, dimethylacetamide, ethyl acetate, hexane, acetonitrile, and the like, preferably dichloroethane, which are used alone or in combination. Examples of the suitable sulfur compound include ethanethiol, dimethyl sulfide, benzenethiol, and the like. Examples of the suitable Lewis acid include a boron trifluoride diethyl ether complex, aluminum trichloride, titanium tetrachloride, tin tetrachloride, and the like, and a preferred example is a boron trifluoride diethyl ether complex. Alternatively, this step can be carried out by treating with a Lewis acid in the absence of the sulfur compound. Examples of the Lewis acid usable in the absence of the sulfur compound include boron tribromide, boron trichloride, trimethylsilyl iodide, dimethylboron bromide, and the like, and a preferred example is boron tribromide. The solvent, reaction temperature and reaction time to be used are similar to those described above.

The intermediates and objective compounds in the above-described production methods can be isolated and purified by subjecting them to the separation and purification methods usually used in the synthetic organic chemistry, such as filtration, extraction, washing, drying, concentration, recrystallization, various kinds of chromatography or the like. In the case of the intermediates, they can also be applied to the subsequent reactions without purification.

When it is desired to obtain a salt of Compound (I), in the case where Compound (I) is produced in the form of the salt, it can be purified as it is, but in the case where it is produced in its free form, it can be dissolved or suspended in a suitable solvent, converted into a salt by adding an acid or base and then the resulting salt can be isolated and purified. Furthermore, Compound (I) or pharmaceutically acceptable salts thereof may exist in the form of adducts with water or various solvents, and these adducts are also included in the present invention.

Specific examples of Compound (I) obtained by the present invention are shown in Table 1.

TABLE 1

| Compound No. | G |
|---|---|
| 1 | |
| 2 | |

TABLE 1-continued

| Compound No. | G |
|---|---|
| 3 | |
| 4 | |
| 5 | |
| 6 | |
| 7 | |
| 8 | |
| 9 | |
| 10 | |

TABLE 1-continued
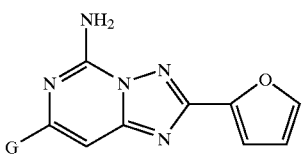
| Compound No. | G |
|---|---|
| 11 | 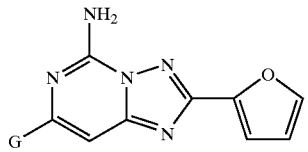 |
| 12 | 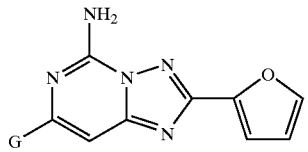 |
| 13 | 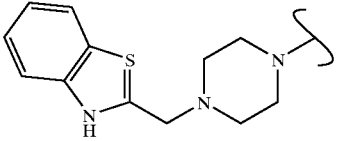 |
| 14 | 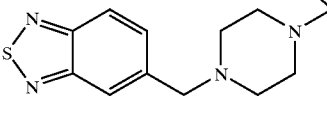 |
| 15 | 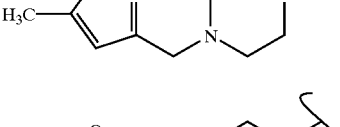 |
| 16 | 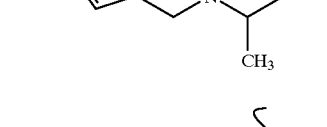 |
| 17 | 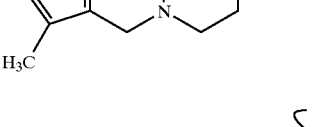 |
| 18 | 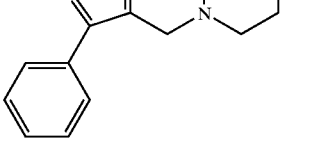 |
TABLE 1-continued
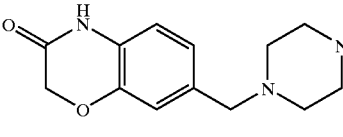
| Compound No. | G |
|---|---|
| 19 | 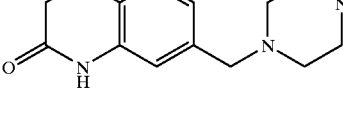 |
| 20 | 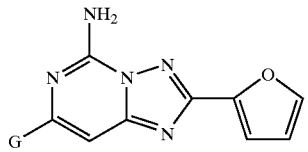 |
| 21 | 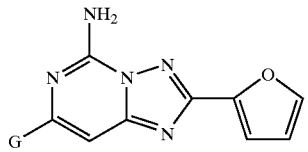 |
| 22 | 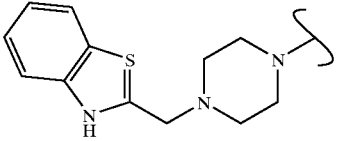 |
| 24 | 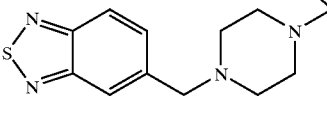 |
| 25 | 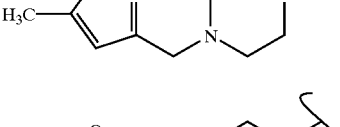 |
| 26 | 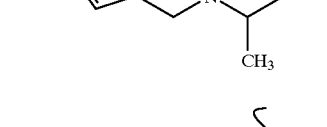 |
| 27 | 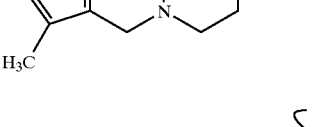 |

TABLE 1-continued

Compound No. G

28

Next, pharmacological activities of Compound (I) are illustrated with reference to Test Examples.

Test Example 1

Adenosine Receptor Binding Activity (Adenosine $A_{2A}$ Receptor Binding Test)

This test was carried out in a similar manner to the method of Bruns et al. (*Molecular Pharmacology*, 29: 331 (1986)).

Corpus striatum of a rat was suspended in an ice-cooled 50 mmol/L tris(hydroxymethyl)aminomethane hydrochloride (hereinafter referred to as "Tris-HCl") buffer (pH 7.7) using Polytron Homogenizer (manufactured by Kinematica Co.) The suspension was centrifuged (50,000×g, 10 minutes), the obtained precipitate was re-suspended in the same amount of 50 mmol/L Tris-HCl buffer, and then, the suspension was centrifuged similarly. The final precipitate was suspended in 50 mmol/L Tris-HCl buffer (containing 10 mmol/L magnesium chloride and 0.02 unit/mg tissue of adenosine deaminase (manufactured by Sigma Co.)) by adding the buffer to the final precipitate so as to give a tissue concentration of 5 mg (wet weight)/mL.

To 1 mL of the tissue suspension thus prepared, 50 µL (final concentration: 4.0 mmol/L) of tritium-labeled CGS 21680 {$^3$H-2-[p-(2-carboxyethyl)phenethylamino]-5'-(N-ethylcarboxamido)adenosine: 40 Ci/mmol; manufactured by New England Nuclear Co. (*The Journal of Pharmacology and Experimental Therapeutics*, 251: 888 (1989))} and 50 µL of a test compound were added. The resulting mixture was allowed to stand for 120 minutes at 25° C., and then rapidly filtered by suction through a glass fiber filter (GF/C, manufactured by Whatman Co.) The glass fiber filter was immediately washed three times with 5 µL of an ice-cooled 50 mmol/L Tris-HCl buffer, and transferred to a vial, a scintillator (EX-H, manufactured by Wako Pure Chemical Industries, Ltd.) was added thereto, and the radioactivity on the filter was determined with a liquid scintillation counter (manufactured by Packard Instrument Co.)

An inhibition ratio of each test compound against $A_{2A}$ receptor binding ($^3$H-CGS 21680 binding) was calculated by the following equation:

Inhibition ratio (%)={1−(amount of the binding in the presence of the test compound−amount of the non-specific binding)/(amount of the total binding−amount of the non-specific binding)}×100

(Note) Amount of the total binding is the amount of the $^3$H-CGS 21680 bonded radioactivity in the absence of the test compound. Amount of the non-specific binding means the amount pf the $^3$H-CGS 21680 bonded radioactivity in the presence of 100 mmol/L cyclopentyladenosine (CPA, manufactured by Sigma Co.) Amount of the binding in the presence of the test compound is the amount of 3H-CGS 21680 bonded radioactivity in the presence of the test compound in a varied concentration.

The results are shown in Table 2.

TABLE 2

| Compound No. | Rat $A_{2A}$ receptor inhibition ratio (%) | |
| --- | --- | --- |
| | $10^{-6}$ mol/L | $10^{-7}$ mol/L |
| 1 | 81 | 42 |
| 2 | 84 | — |
| 3 | 93 | — |
| 7 | 81 | — |
| 8 | 84 | — |
| 9 | 89 | — |
| 10 | 87 | — |
| 11 | 88 | — |
| 15 | 92 | — |
| 16 | 88 | — |
| 17 | 90 | — |
| 18 | 96 | — |
| 19 | 95 | — |
| 21 | 90 | 65 |
| 22 | 84 | — |
| 23 | 75 | — |
| 24 | 96 | — |
| 25 | 95 | — |
| 26 | 94 | — |
| 27 | 96 | — |

From Table 2, Compounds (I) show strong adenosine $A_{2A}$ receptor antagonism, and therefore, it was suggested that a medicament which contains Compound (I) as the active ingredient would be useful for various diseases induced by hyperactivity of an adenosine $A_{2A}$ receptor (for example, Parkinson's disease, senile dementia or depression).

Test Example 2

Activity on CGS 21680-induced Catalepsy

Parkinson's disease is a motor deficit based on the degeneration and cell death of the nigrostriatal dopaminergic neuron. When CGS 21680 (adenosine $A_{2A}$ receptor agonist) is administered into the intracerebro-ventricle, it directly inhibits inhibitory synaptic transmission of GABA in medium sized spiny neuron in the striatum via the adenosine $A_{2A}$ receptor. (*Journal of Neuroscience*, 16: 605 (1996)). Accordingly, it is considered that adenosine $A_{2A}$ receptor agonists positively regulate the output of the striopallidal GABAergic neurons and, as a result, catalepsy is induced by the administration of CGS 21680.

This test was carried out using 10 animals per group of male ddY mice of 5 week age (22 to 25 g in body weight, Japan SLC). CGS 21680 (manufactured by RBI) was dissolved in physiological saline (manufactured by Otsuka Pharmaceutical Co., Ltd.), and 10 µg/20 µL of the solution was injected into mouse intracerebro-ventricle. Test compounds were used by suspending them in distilled water containing 0.5% of methylcellulose (hereinafter referred to as "MC") (manufactured by Otsuka Pharmaceutical Co., Ltd.) The suspension containing each of the test compounds or a solution containing no test compound (distilled water containing 0.5% MC, as a control) was orally administered (0.1 mL per 10 g mouse body weight) 30 minutes before the injection of CGS 21680 into the intracerebro-ventricle. One hour after the administration of the test compound, only forelimbs or only hindlimbs of each animal were laid on a vertically arranged stand made of acryl, having a size of 4.5 cm in height and 1.0 cm in width, to measure catalepsy symptoms. All of the test compounds were administered orally in a dose of 10 mg/kg. Table 3 shows the judging criteria of the catalepsy score.

TABLE 3

| Score | Duration of catalepsy |
|---|---|
| 0 | The cataleptic posture lasted less than 5 seconds for both forelimbs and hindlimbs. |
| 1 | (1) The cataleptic posture of forelimbs lasted 5 seconds or more and less than 10 seconds, and that of hindlimbs lasted less than 5 seconds, or (2) The cataleptic posture of forelimbs lasted less than 5 seconds, and that of hindlimbs lasted 5 seconds or more and less than 10 seconds. |
| 2 | The cataleptic posture of forelimbs lasted 10 seconds or more and that of hindlimbs lasted less than 5 seconds. |
| 3 | (1) The cataleptic posture of both forelimbs and hindlimbs lasted 5 seconds or more and less than 10 seconds, or (2) The cataleptic posture of forelimbs lasted less than 5 seconds but that of hindlimbs lasted 10 seconds or more. |
| 4 | (1) The cataleptic posture of forelimbs lasted 10 seconds or more and that of hindlimbs lasted 5 seconds or more and less than 10 seconds, or (2) The cataleptic posture of forelimbs lasted 5 seconds or more and less than 10 seconds, and that of hindlimbs lasted 10 seconds or more. |
| 5 | The cataleptic posture of both forelimbs and hindlimbs lasted 10 seconds or more. |

The effect was judged by total catalepsy scores of 10 animals in one group (the maximum score is 50 points). When total score was 40 points or less, the activity of the compounds was judged positive. The number of animals showing remission of catalepsy was expressed by the number of cases in which the catalepsy score was 4 points or less in 10 cases. The catalepsy remission ratio was expressed as the percentage reduction of the total score in the test compound-administered group to the total score in the control group.

The results are shown in Table 4.

TABLE 4

| Compound No. | Number of animals used | Total score | Number of animals showing remission | Remission ratio (%) |
|---|---|---|---|---|
| 0.5% MC (control) | 10 | 50 | 0 | 0 |
| 1 | 10 | 0 | 10 | 100 |
| 5 | 10 | 5 | 10 | 90 |
| 6 | 10 | 8 | 10 | 84 |
| 7 | 10 | 8 | 9 | 84 |
| 10 | 10 | 11 | 9 | 78 |
| 13 | 10 | 10 | 8 | 80 |
| 14 | 10 | 9 | 9 | 82 |
| 19 | 10 | 5 | 9 | 90 |
| 20 | 10 | 5 | 9 | 90 |
| 21 | 10 | 0 | 10 | 100 |
| 22 | 10 | 1 | 10 | 98 |
| 24 | 10 | 2 | 10 | 96 |
| 27 | 10 | 4 | 9 | 92 |

Test Example 3

Activity on Haloperidol-induced Catalepsy

Parkinson's disease is a disease based on the degeneration and cell death of the nigrostriatal dopaminergic neuron. When haloperidol (dopamine $D_2$ antagonist) is administered, catalepsy is induced by the block of postsynaptic $D_2$ receptor. This haloperidol-induced catalepsy is known as a classic model in which symptoms of Parkinson's disease are produced by drug administration (*European Journal of Pharmacology*, 182: 327 (1990) and U.S. Pat. No. 3,991,207).

This test was carried out using 10 animals per group of male ddY mice of 5 week age (22 to 24 g in body weight, Japan SLC). Haloperidol (manufactured by Janssen) was suspended in 0.5% MC and administered intraperitoneally into mice at a dose of 1.0 mg/kg. Each test compound was suspended in distilled water for injection containing 0.5% MC (manufactured by Otsuka Pharmaceutical Co., Ltd.) (10 mg/kg). Also, as a control drug, 100 mg/kg of L-DOPA and 25 mg/kg of benserazide were used as a solution by dissolving them into distilled water for injection containing 0.5% MC (manufactured by Otsuka Pharmaceutical Co., Ltd.) One hour after the intraperitoneal injection of haloperidol, the suspension containing each of the test compounds or the solution containing the control drug was orally administered (0.1 mL per 10 g mouse body weight) and, one hour after the administration of the test compound or the control drug, only forelimbs or only hindlimbs of each animal were laid on a stand having a size of 4.5 cm in height and 1.0 cm in width, to measure catalepsy symptoms. The catalepsy score was evaluated by the judging criteria shown in the above-described Table 3.

The effect was judged by total catalepsy scores of 10 animals in one group (the maximum score is 50 points). When the total score was 40 points or less, the activity of the test compounds was judged positive. The number of animals showing remission of catalepsy was expressed by the number of cases in which the catalepsy score was 4 points or less in 10 cases. The catalepsy remission ratio was expressed as the percentage reduction of the total score in the test compound-administered group to the total score in the control group.

The results are shown in Table 5.

TABLE 5

| Compound No. | Number of animals used | Total score | Number of animals showing remission | Remission ratio (%) |
|---|---|---|---|---|
| 0.5% MC (control) | 10 | 50 | 0 | 0 |
| 1 | 10 | 0 | 10 | 100 |
| 21 | 10 | 0 | 10 | 100 |

Test Example 4

Activity on Reserpine-induced Catalepsy

Catalepsy induced by the administration of an antipsychotic agent such as reserpine is known as a useful symptom model of Parkinsonism (*Journal of Neural Transmission*, 8: 39–71 (1994)).

This test was carried out using 10 animals per group of male ddY mice of 5 week age (22 to 24 g in body weight, Japan SLC). During the preliminary feeding period, they were allowed to have feed and water freely in an animal room of a room temperature of 23±1° C. and a humidity of 55±5%. Reserpine (5 mg/kg: apoplon, Daiichi Pharmaceutical Co., Ltd.; diluted with distilled water) was subcutaneously administered, and catalepsy-inducing activity was observed from 18 hours after the administration. The mice showing catalepsy score of 5 (judging criteria in Table 3 of Test Example 2) were selected and used in the experiment. Each test compound was suspended in distilled water for injection containing 0.5% MC (manufactured by Otsuka Pharmaceutical Co., Ltd.) The suspension containing each of the test compounds or a solution containing no test compound (distilled water for injection containing 0.5% MC (manufactured by Otsuka Pharmaceutical Co., Ltd.); control) was orally administered (0.1 mL per 10 g mouse body weight) and, one hour after the administration of test compound, only forelimbs or only hindlimbs of each animal were laid on a stand having a size of 4.5 cm in height and 1.0 cm in width, to measure catalepsy symptoms.

The effect was judged by total catalepsy scores of 10 animals in one group (the maximum is 50 points). When the total score was 40 points or less, the activity of the test compound was judged positive. The number of animals showing remission of catalepsy was expressed by the number of cases in which the catalepsy score was 4 points or less in 10 cases. The catalepsy remission ratio was expressed as the percentage reduction of the total score in the test compound-administered group to the total score in the control group.

The results are shown in Table 6.

TABLE 6

| Compound No. | Number of Animals used | Total score | Number of animals showing remission | Remission ratio (%) |
|---|---|---|---|---|
| 0.5% MC (control) | 10 | 50 | 0 | 0 |
| 1 | 10 | 14 | 8 | 72 |
| 5 | 10 | 12 | 10 | 76 |
| 6 | 10 | 11 | 9 | 78 |
| 7 | 10 | 23 | 7 | 54 |
| 14 | 10 | 12 | 8 | 76 |
| 19 | 10 | 19 | 7 | 62 |
| 21 | 10 | 17 | 7 | 66 |
| 22 | 10 | 13 | 10 | 74 |
| 24 | 10 | 14 | 9 | 72 |

Test Example 5

Activity in Parkinson's Disease Model (Common Marmoset Treated with 1-methyl-4-phenyl-1,2,3,6-tetrahydropyridine (MPTP))

Parkinson's disease is a disease based on the degeneration and cell death of the nigrostriatal dopaminergic neuron. In the primates, treatment with a dopamine neurotoxin 1-methyl-4-phenyl-1,2,3,6-tetrahydropyridine (hereafter referred to as "MPTP") causes selective degeneration and drop out of the nigrostriatal dopaminergic neuron and shows akinesia and rigidity of muscle or the like. These MPTP-treated primates are known as a model of Parkinson's disease (*Proceedings of the National Academy of Science USA*, 80: 4546 (1983)). Common marmoset belongs to Anthropoidae, and it is known that it shows symptoms of Parkinson's disease caused by MPTP as in the case of other animals of Anthropoidae [*Neuroscience Letter*, 57: 37 (1985)].

This test was carried out using 4 animals per group of female and male common marmosets of 2 to 3 year age (300 to 375 g in body weight, CLEA Japan). MPTP (manufactured by RBI) was dissolved in physiological saline for injection (manufactured by Otsuka Pharmaceutical Co., Ltd.) and administered to common marmoset once a day for 5 days by subcutaneous injection in a dose of 2.0 mg/kg. Six weeks or more after the administration, animals showing chronic symptoms of Parkinson's disease were used in the test. Each test compound was used by suspending it in 0.3% Tween 80 and 10% sucrose solution. One hour before the administration of the test compound, the animals to be tested were put into an observation cage (equipped with a spontaneous locomotor count measuring apparatus) to adapt them to the environment. Pre-motor disability before administration of the test compound was scored, and was compared with the motor disability score after administration of the test compound. Symptoms of Parkinson's disease were observed from a one way see through window at 30 minutes' interval for 8 hours to score their motor disability. The spontaneous locomotor count was measured at 30 minutes' interval for 12 hours by a computer-controlled automatic measuring apparatus. Symptoms of Parkinson's disease were judged based on the judging criteria of each observation item shown below, and the total of the points was used as the score of each animal.

Relationship between observation items and scores is shown in Table 7 below.

TABLE 7

| Items observed | Score | 0 | 1 | 2 | 3 | 4 |
|---|---|---|---|---|---|---|
| Attention | | Normal | Decrease | Sleeping tendency | | |
| Observation | | | Yes | Decrease | No | |
| Blinking | | | Normal | Abnormal | | |
| Posture | | Normal | Abnormality in trunk, tail or limbs (1 point for each) | | | All abnormal |
| Balance | | Normal | Asymmetry | Cannot stand | Drop out | |
| Reaction | | Normal | Decrease | Slow | No | |
| Utterance | | Normal | Decrease | No | | |
| Total | 0–17 points | | | | | |

The effect was judged by comparing average scores of the symptoms of Parkinson's disease in 4 animals per group before and after the administration of the test compound (significance test: Wilcoxon Rank Sum test).

The results are shown in Table 8.

TABLE 8

| Compound No. | Average score before administration | Average score at maximum improvement after administration |
|---|---|---|
| 1 | 12.75 ± 0.25 | 4.75 ± 0.48 ($p < 0.0256$) |

In addition to Compound 1, it was also revealed that Compounds 7, 21, 22 and 24 were effective in the common marmoset MPTP-treated Parkinson's disease model.

As described above, anti-Parkinson's disease activity of Compounds (I) was confirmed from Test Examples 2 to 5.

Test Example 6

Forced Swimming Method (Measurement of Immobility Time)

Ten animals per group of ddY male mice (21 to 26 g in body weight, Japan SLC) were used as the test animal.

During the preliminary feeding period, they were allowed to have feed and water freely in an animal room of a room temperature of 23±1° C. and a humidity of 55±5%. Animals showing abnormal reactions in terms of spontaneous activity, myotonia, eyesight or the like were excluded beforehand. The test compound was suspended in a 0.3% Tween 80 solution and orally administered one hour before the test. In the negative control group, 10 mL/kg of a 0.3% Tween 80 solution alone was orally administered. Measurement of immobility time was carried out in accordance with the method of Porsolt (*Arch. int Pharmacodyn.*, 229: 327–336 (1977)). That is, a cylindrical transparent acrylic water tank (10 cm in diameter and 25 cm in height) was filled with 9 cm in depth of water having a temperature of 23±1° C., and mice were forced to swim for 6 minutes. When mice are put into water, they immediately start to swim trying to escape from the tank, but the motion gradually decreases 1 to 2 minutes thereafter. Measurement of immobility time was carried out by leaving them for 2 minutes as such and then measuring the period of time during which they did not show the escaping action (immobility time: behavioral despair) for 4 minutes (240 seconds) at at one second's interval. In order to reduce effects of daily rhythm, the test was carried out by using 5 of the 10 animals per group in the morning, and the remaining 5 animals in the afternoon. Also, measurement of immobility time was carried out by observing 2 animals at the same time and by not telling the observers distinctions about the solvent alone-administered group and doses of the test compound. Statistical analysis of the results was carried out by a multiple comparison test between the solvent-administered control group and the test compound-administered group by Steel-test.

The results are shown in Table 9.

TABLE 9

| Test compound | Immobility time (second) |
|---|---|
| 0.5% MC (negative control) | 180.3 ± 15.3 |
| 21 | 7.6 ± 3.2 (p < 0.01) |

Also, significant immobility time-shortening activity was observed by 10 mg/kg oral administration of Compound 1.

From Test Example 6, anti-depression activity of Compounds (I) was shown.

Compound (I) or a pharmaceutically acceptable salt thereof can be administered as it is, but it is generally preferred to provide it as various pharmaceutical preparations. Furthermore, such pharmaceutical preparations are used in animals and human.

The pharmaceutical preparations of the present invention can contain Compound (I) or a pharmaceutically acceptable salt thereof as the active ingredient alone or together with other optional active ingredients for the treatment of different diseases. Furthermore, these pharmaceutical preparations are produced by optional methods well known in the technical field of pharmaceutics, by mixing the active ingredient with one or more pharmaceutically acceptable carriers.

It is preferred to select a route of administration which is most effective in the treatment. Examples include oral administration and parenteral administrations, such as intraoral, endotracheal, rectal, subcutaneous, intramuscular, intravenous, and the like.

Examples of the dosage form include sprays, capsules, tablets, granules, syrups, emulsions, suppositories, injections, ointments, tapes, and the like.

Liquid preparations, such as emulsions, syrups, and the like, suitable for oral administration can be produced using, for example, water; sugars, such as sucrose, sorbitol, fructose, and the like; glycols, such as polyethylene glycol, propylene glycol, and the like; oils, such as sesame oil, olive oil, soybean oil, and the like; antiseptics, such as p-hydroxybenzoic acid esters, and the like; flavors, such as strawberry flavor, peppermint, and the like; and so forth. Furthermore, capsules, tablets, powders, granules and the like can be produced using, for example, excipients, such as lactose, glucose, sucrose, mannitol, and the like; disintegrators, such as starch, sodium alginate, and the like; lubricants, such as magnesium stearate, talc, and the like; binders, such as polyvinyl alcohol, hydroxypropyl cellulose, gelatin, and the like; surfactants, such as fatty acid esters, and the like; plasticizers, such as glycerol, and the like; and so forth.

Preparations suitable for parenteral administration are preferably sterile aqueous preparations which contain an active compound that becomes isotonic in the blood of acceptors. For example, in the case of injections, a solution for injection is prepared using a carrier comprising a salt solution, a glucose solution or a mixture of salt water with a glucose solution. In that case, the injections are prepared in the form of a solution, suspension or dispersion in the usual way using a suitable auxiliary agent. Preparations for rectal administration are prepared using a carrier, such as cacao butter, hydrogenated fat, hydrogenated carboxylic acid or the like, and provided as suppositories. Furthermore, sprays are prepared using an active compound alone or the active compound and a carrier which does. not stimulate the oral cavity and airway mucous membrane of the acceptors and can facilitate absorption of the active compound by dispersing it in fine particles. Specific examples of the carrier include lactose, glycerol and the like. Preparations, such as aerosols, dry powders and the like, can be produced depending on the properties of the active compound and the carriers to be used.

Additionally, these parenteral preparations can also be mixed with one or more auxiliary components selected from the diluents, flavors, antiseptics, excipients, disintegrators, lubricants, binders, surfactants, plasticizers and the like exemplified in relation to the oral preparations.

The effective amount of Compound (I) or a pharmaceutically acceptable salt thereof and the frequency of its administration vary depending on the administration mode, the age and body weight of each patient and properties and seriousness of the symptoms to be treated, but it is generally preferred to administer it in a dose of from 1 to 50 mg/kg per day, by dividing the daily dose into 3 or 4 doses per day. However, these doses may vary depending on the above-described various conditions.

Best Mode For Carrying Out the Invention

Reference Examples, Examples and Formulation Examples are shown below. In proton nuclear magnetic resonance spectrum ($^1$H NMR) used in Reference Examples and Examples, conventional symbols are used for expressing signal multiplicity, and a symbol "br" means that apparent broad signals were measured.

Reference Example 1

N-(4-Chloro-2-methylthiopyrimidin-6-yl)-N'-(2-furoyl)hydrazine (Compound A)

Into 150 mL of DMF, 65 g (515 mmol) of 2-furoic hydrazide and 70 mL (510 mmol) of DBU were dissolved, and a DMF solution of 4,6-dichloro-2-methylthiopyrimidine (50.0 g (256 mmol)/100 mL) was slowly added dropwise thereto at room temperature (inner temperature was controlled at 45° C. or lower). After stirring at room temperature for about 2 hours, the reaction solution was poured into ice-water and the pH was adjusted to 6 to 7 with a 2 mol/L hydrochloric acid solution, followed by collecting the resulting solid through filtration. The collected solid was dissolved into an organic solvent (chloroform/methanol=10/1) and, after washing with water, the solution was dried over anhydrous magnesium sulfate. The solvent was evaporated, and the resulting residue was triturated twice with chloroform to obtain 56.9 g of Compound A as white flocculent crystals (yield: 78%). The residue obtained by concentrating the filtrate was purified by silica gel column chromatography (hexane/ethyl acetate=6/4) to additionally recover Compound A in about 10% yield.

$^1$H NMR (δ ppm, DMSO-d$_6$): 10.49 (brs, 1H), 9.78 (brs, 1H), 7.95 (dd, J=0.7, 1.7 Hz, 1H), 7.28 (dd, J=0.7, 3.3 Hz, 1H), 6.70 (dd, J=1.7, 3.3 Hz, 1H), 6.30 (brs, 1H), 2.50 (brs, 3H)

Mass (m/z): 284, 286 (M$^+$)

IR (KBr): 3750, 1654, 1560, 1478 cm$^{-1}$

Melting point: 185° C.

Reference Example 2

7-Chloro-3-(2-furyl)-5-methylthio[1,2,4]triazolo [4,3-c]pyrimidine (Compound B)

In an argon atmosphere, 225 g (1.58 mol) of diphosphorus pentaoxide was suspended in 320 mL of xylene, and 340 mL (256 g, 1.58 mol) of hexamethyldisiloxane was added thereto, followed by heating at 90° C. for about 1.5 hours. After the contents were almost dissolved, 90 g (316 mmol) of Compound A was added thereto, followed by heating at 160° C. for another 2 hours. After completion of the reaction, the reaction solution was cooled, and ice-water was added thereto. Then, the mixture was made alkaline by adding aqueous ammonia under cooling (inner temperature: 5° C. or lower), and was extracted with chloroform. After evaporation of the solvent, the residue was purified by silica gel column chromatography (hexane/ethyl acetate=1:1) to obtain 66.1 g of Compound B as a white solid (yield: 78%).

$^1$H NMR (δ ppm, CDCl$_3$): 7.75 (dd, J=0.7, 1.7 Hz, 1H), 7.44 (s, 1H), 6.97 (dd, J=0.7, 3.3 Hz, 1H), 6.66 (dd, J 1.7, 3.3 Hz, 1H), 2.63 (s, 3H)

Mass (m/z): 266, 268 (M$^+$)

IR (KBr): 3040, 1592, 1512, 1464, 1301, 1081, 1009, 902, 897, 755 cm$^{-1}$

Melting point: 122–124° C.

Reference Example 3

7-Chloro-2-(2-furyl)-5-methylthio[1,2,4]triazolo [1,5-c]pyrimidine (Compound C)

Into 8.5 mL of THF, 2.7 g (10 mmol) of Compound B was dissolved, and 1.5 mL (10 mmol) of DBU was added thereto under ice cooling, followed by stirring at room temperature for about 1 hour. During the period, crystals were precipitated from the reaction solution. After completion of the reaction, the precipitated solid was washed with THF to obtain 2.1 g of Compound C as a white solid (yield: 81%).

$^1$H NMR (δ ppm, CDCl$_3$): 7.65 (dd, J=0.7, 1.7 Hz, 1H), 7.36 (s, 1H), 7.28 (dd, J=0.7, 3.3 Hz, 1H), 6.60 (dd, J=1.7, 3.3 Hz, 1H), 2.78(s, 3H)

Mass (m/z): 266, 268 (M$^+$)

IR (KBr): 3745, 1596, 1508, 1452 cm$^{-1}$

Melting point: 230° C.

Reference Example 4

7-Chloro-5-(3,4-dimethoxybenzylamino)-2-(2-furyl) [1,2,4]triazolo[1,5-c]pyrimidine (Compound D)

Into 600 mL of THF, 50.0 g (188 mmol) of Compound B was dissolved, and 42.0 mL (280 mmol) of DBU was added thereto, followed by stirring at room temperature for about 30 minutes. During the period, crystals were precipitated from the reaction solution. Next, 94 g (563 mmol) of 3,4-dimethoxybenzylamine was added thereto, followed by stirring at 60° C. for about 2 hours. After completion of the reaction, the solvent was evaporated, the residue was diluted with chloroform and washed with water, and the organic layer was dried over magnesium sulfate. The solvent was evaporated, and the resulting residue was triturated with ethyl acetate to obtain 53.2 g of Compound D as a white solid (yield: 74%). The residue obtained by concentrating the solution part present after trituration was purified by silica gel column chromatography (hexane/ethyl acetate=7/3) to additionally recover Compound D in about 10% yield.

$^1$H NMR (δ ppm, CDCl$_3$): 7.60 (dd, J=0.7, 1.7 Hz, 1H), 7.20 (dd, J=0.7, 3.3 Hz, 1H), 6.94–6.98 (m, 3H), 6.85 (d, J=7.9 Hz, 1H), 6.61 (brt, 1H), 6.58 (dd, J=1.7, 3.3 Hz, 1H), 4.74 (d, J=5.6 Hz, 2H), 3.90 (s, 3H), 3.89 (s, 3H)

Mass (m/z): 385, 387 (M$^+$)

IR (KBr): 2359, 1630, 1616, 1585, 1515 cm$^{-1}$

Melting point: 193° C.

Reference Example 5

5-Amino-7-chloro-2-(2-furyl)[1,2,4]triazolo [1,5-c]pyrimidine (Compound E)

Into 260 mL of trifluoroacetic acid, 50.0 g (130 mmol) of Compound D was dissolved, and 50 g (333 mmol) of trifluoromethanesulfonic acid and 42 mL (390 mmol) of anisole were added thereto, followed by stirring at room temperature for about 2 hours. After completion of the reaction, trifluoroacetic acid was evaporated under reduced pressure, and the residue was poured into ice-water. The mixture was adjusted to be alkaline with a 2 mol/L aqueous sodium hydroxide solution. The precipitated solid was washed with hexane and was reslurried with chloroform to obtain 25.6 g of Compound E as a white solid (yield: 83%).

$^1$H NMR (δ ppm, CDCl$_3$): 7.64 (dd, J=0.7, 1.7 Hz, 1H), 7.25 (dd, J=0.7, 3.3 Hz, 1H), 7.04 (s, 1H), 6.60 (dd, J=1.7, 3.3 Hz, 1H), 6.30 (brs, 2H)

Mass (m/z): 235, 237 (M$^+$)

IR (KBr): 3104, 3070, 1666, 1592, 1552, 933 cm$^{-1}$

Melting point: >270° C.

Reference Example 6

5-Amino-2-(2-furyl)-7-piperazinyl[1,2,4]triazolo [1,5-c]pyrimidine (Compound F)

Into 180 mL of DMSO, 10.5 g (44.6 mmol) of Compound E and 19.2 g (223 mmol) of piperazine were dissolved, followed by stirring at 150° C. for about 2 hours. After completion of the reaction, the solvent was evaporated under reduced pressure, water was added to the residue, and the mixture was extracted with chloroform. The organic layer was washed with water and brine, and then dried over anhydrous magnesium sulfate. After evaporation of the solvent, the resulting residue was purified by silica gel column chromatography (23% aqueous ammonia/methanol/chloroform=1/10/90) and then recrystallized from ethyl acetate to obtain 9.91 g of Compound F as a white solid (yield: 78%).

$^1$H NMR (δ ppm, DMSO-d$_6$): 7.86 (dd, J=0.7, 1.7 Hz, 1H), 7.60 (brs, 2H), 7.06 (dd, J=0.7, 3.3 Hz, 1H), 6.68 (dd, J=1.7, 3.3 Hz, 1H), 6.01 (s, 1H), 3.49 (t, J=5.0 Hz, 4H), 3.40 (brs, 2H), 2.83 (t, J=5.0 Hz, 4H)

Mass (m/z): 285 (M$^+$)

IR (KBr): 1656, 1650, 1614, 1555, 1514, 1234 cm$^{-1}$

Melting point: 170–172° C.

EXAMPLE 1

5-Amino-2-(2-furyl)-7-(4-(2-hydroxy-2-methylpropyl)piperazinyl)[1,2,4]triazolo [1,5-c]pyrimidine (Compound 1)

Into 7 mL of DMSO, 500 mg (2.12 mmol) of Compound E was dissolved, and then 0.95 mL (6.36 mmol) of DBU and 1.50 g (9.50 mmol) of 1-($^2$-hydroxy-2-methylpropyl) piperazine were added thereto, followed by stirring at 140° C. for about 2 hours. After completion of the reaction, the reaction mixture was extracted by adding chloroform and water, and the organic layer was washed with water and brine, and then dried over anhydrous magnesium sulfate. After evaporation of the solvent, the resulting residue was purified by silica gel column chromatography (3% methanol-chloroform) and then recrystallized from a mixed solvent of hexane-ethyl acetate to obtain 250 mg of Compound 1 as a white solid (yield: 33%).

$^1$H NMR (δ ppm, CDCl$_3$): 7.58 (dd, J=0.7, 1.7 Hz, 1H), 7.16 (dd, J=0.7, 3.3 Hz, 1H), 6.55 (dd, J=1.7, 3.3 Hz, 1H), 6.02 (s, 1H), 5.71 (brs, 2H), 3.55 (t, J=5.0 Hz, 4H), 2.96 (brs, 1H), 2.73 (t, J=5.0 Hz, 4H), 2.39 (s, 2H), 1.21 (s, 6H)

Mass (m/z): 357 (M$^+$)

IR (KBr): 3853, 1678, 1608, 1558, 1471, 1331 cm$^{-1}$

Melting point: 235–236° C.

Elemental analysis: as C$_{27}$H$_{23}$N$_7$O$_2$ Calculated (%): C=57.13; H=6.49; N=27.43; Found (%): C=57.28; H=6.58; N=27.48.

Compounds 2 to 14 were obtained by carrying out the following Examples 2 to 14 using corresponding piperazine derivatives in a manner similar to that in Example 1.

EXAMPLE 2

5-Amino-2-(2-furyl)-7-(4-(2-hydroxy-2-methylbutyl)piperazinyl)[1,2,4]triazolo [1,5-c]pyrimidine (Compound 2)

Yield: 54% (recrystallized from toluene-hexane; pale brown needles)

$^1$H NMR (δ ppm, CDCl$_3$): 7.59 (dd, J=0.7, 1.7 Hz, 1H), 7.16 (dd, J=0.7, 3.3 Hz, 1H), 6.56 (dd, J=1.7, 3.3 Hz, 1H), 6.02 (s, 1H), 5.63 (brs, 2H), 3.55 (t, J=5.0 Hz, 4H), 2.73 (t, J=5.0 Hz, 4H), 2.44 (d, J=13.9 Hz, 1H), 2.34 (d, J=13.9 Hz, 1H), 1.43–1.58 (m, 2H), 1.14 (s, 3H), 0.92 (t, J=7.59 Hz, 3H)

Mass (m/z): 371 (M$^+$)

IR (KBr): 3319, 3176, 2970, 2833, 1655, 1614, 1606, 1557, 1513, 1444, 1333, 1236 cm$^{-1}$

Melting point: 212° C.

Elemental analysis: as C$_{18}$H$_{25}$N$_7$O$_2$ 0.4toluene Calculated (%): C=61.19; H=6.96; N=24.01; Found (%): C=61.36; H=7.06; N=23.93.

EXAMPLE 3

5-Amino-2-(2-furyl)-7-(4-(2-hydroxy-2-phenylpropyl)piperazinyl)[1,2,4]triazolo [1,5-c]pyrimidine (Compound 3)

Yield: 34% (recrystallized from ethanol-toluene; white powder)

$^1$H NMR (δ ppm, CDCl$_3$): 7.57 (dd, J=0.7, 1.7 Hz, 1H), 7.48 (d, J=7.3 Hz, 1H), 7.35(t, J=7.59 Hz, 1H), 7.25 (d, J=6.6 Hz, 1H), 7.14 (dd, J=0.7, 3.3 Hz, 1H), 6.55 (dd, J=1.7, 3.3 Hz, 1H), 5.94 (s, 1H), 5.56 (brs, 2H), 4.25 (s, 1H), 3.42 (t, J=5.0 Hz, 4H), 2.90 (d, J=13.0 Hz, 1H), 2.68 (d, J=13.0 Hz, 1H), 2.32–2.52 (m, 4H), 1.50 (s, 3H)

Mass (m/z): 419 (M$^+$)

IR (KBr): 3333, 3176, 2361, 1664, 1647, 1603, 1560, 1442, 1417, 1334, 1225, 1007, 770 cm$^{-1}$

Melting point: 267–268° C.

Elemental analysis: as C$_{22}$H$_{25}$N$_7$O$_2$ Calculated (%): C=62.99; H=6.01; N=23.37; Found (%): C=63.04; H=6.25; N=23.58.

EXAMPLE 4

5-Amino-2-(2-furyl)-7-(4-(2-ethyl-2-hydroxybutyl) piperazinyl)[1,2,4]triazolo[1,5-c]pyrimidine (Compound 4)

Yield: 71% (recrystallized from toluene-hexane; pale brown needles)

$^1$H NMR (δ ppm, CDCl$_3$): 7.58 (dd, J=0.7, 1.7 Hz, 1H), 7.16 (dd, J=0.7, 3.3 Hz, 1H), 6.55 (dd, J=1.7, 3.3 Hz, 1H), 6.02 (s, 1H), 5.68 (brs, 2H), 3.54 (t, J=5.0 Hz, 4H), 2.91 (brs, 1H), 2.71 (t, J=5.0 Hz, 4H), 1.48 (q, J=7.6 Hz, 4H), 0.88 (t, J=7.6 Hz, 6H)

Mass (m/z): 385 (M$^+$)

IR (KBr): 3410, 3107, 2966, 2951, 2361, 1655, 1616, 1605, 1558, 1446, 1236 cm$^{-1}$

Melting point: 212–213° C.

Elemental analysis: as C$_{19}$H$_{27}$N$_7$O$_2$ Calculated (%): C=59.20; H=7.06; N=25.44; Found (%): C=59.52; H=7.20; N=25.61.

EXAMPLE 5

5-Amino-2-(2-furyl)-7-(4-(1-hydroxycyclopropylmethyl)piperazinyl) [1,2,4]triazolo[1,5-c]pyrimidine (Compound 5)

Yield: 48% (recrystallized from ethanol-ethyl acetate; white powder)

$^1$H NMR (δ ppm, CDCl$_3$): 7.59 (dd, J=0.7, 1.7 Hz, 1H), 7.16 (dd, J=0.7, 3.3 Hz, 1H), 6.56 (dd, J=1.7, 3.3 Hz, 1H), 6.04 (s, 1H), 5.70 (brs, 2H), 3.59 (t, J=5.0 Hz, 4H), 2.70 (t, J=5.0 Hz, 4H), 2.55 (s, 2H), 0.86 (t, J=6.6 Hz, 2H), 0.43 (t, J=6.6 Hz, 2H)

Mass (m/z): 355 (M$^+$)

IR (KBr): 3139, 2833, 2632, 1666, 1614, 1556, 1514, 1443, 1416, 1331, 1243, 1209, 1124, 1016, 771 cm$^{-1}$

Melting point: 215–217° C.

Elemental analysis: as C$_{17}$H$_{21}$N$_7$O$_2$ 0.6H$_2$O Calculated (%): C=55.76; H=6.11; N=26.77; Found (%): C=55.86; H=6.13; N=26.54.

EXAMPLE 6

5-Amino-2-(2-furyl)-7-(4-(2-methoxy-2-methylpropyl)piperazinyl)[1,2,4]triazolo[1,5-c]pyrimidine (Compound 6)

Yield: 70% (recrystallized from ethyl acetate; white powder)

$^1$H NMR (δ ppm, CDCl$_3$): 7.58 (dd, J=0.7, 1.7 Hz, 1H), 7.16 (dd, J=0.7, 3.3 Hz, 1H), 6.55 (dd, J=1.7, 3.3 Hz, 1H), 6.01 (s, 1H), 5.78 (brs, 2H), 3.52 (t, J=5.0 Hz, 4H), 3.22 (s, 3H), 2.65 (t, J=5.0 Hz, 4H), 2.36 (s, 2H), 1.20 (s, 6H)

Mass (m/z): 371 (M$^+$)

IR (KBr): 3417, 3167, 2958, 2833, 2360, 1666, 1608, 1560, 1512, 1470, 1444, 1416, 1381, 1333, 1242, 1132, 1076, 1012 cm$^{-1}$

Melting point: 200–201° C.

Elemental analysis: as C$_{18}$H$_{25}$N$_7$O$_2$ 0.2H$_2$O Calculated (%): C=57.92; H=6.80; N=26.27; Found (%): C=57.86; H=6.92; N=26.24.

EXAMPLE 7

5-Amino-2-(2-furyl)-7-(4-(3-hydroxy-3-methylbutyl)piperazinyl)[1,2,4]triazolo[1,5-c]pyrimidine (Compound 7)

Yield: 59% (recrystallized from toluene-hexane; pale brown powder)

$^1$H NMR (δ ppm, CDCl$_3$): 7.58 (dd, J=0.7, 1.7 Hz, 1H), 7.16 (dd, J=0.7, 3.3 Hz, 1H), 6.55 (dd, J=1.7, 3.3 Hz, 1H), 6.02 (s, 1H), 5.87 (brs, 2H), 3.54 (t, J=5.0 Hz, 4H), 2.68 (t, J=5.9 Hz, 2H), 2.60 (t, J=5.0 Hz, 4H), 1.67 (t, J=5.9 Hz, 2H), 1.25 (s, 6H)

Mass (m/z): 371 (M$^+$)

IR (KBr): 3389, 3107, 2966, 2937, 2837, 1670, 1660, 1639, 1622, 1597, 1549, 1439, 1225 cm$^{-1}$

Melting point: 194–195° C.

Elemental analysis: as C$_{18}$H$_{25}$N$_7$O$_2$ Calculated (%): C=58.21; H=6.78; N=26.40; Found (%): C=58.26; H=7.00; N=26.49.

EXAMPLE 8

5-Amino-2-(2-furyl)-7-(4-(3-hydroxy-3-methylpentyl)piperazinyl)[1,2,4]triazolo[1,5-c]pyrimidine (Compound 8)

Yield: 69% (recrystallized from ethyl acetate-toluene-hexane; brown granular crystals)

$^1$H NMR (δ ppm, CDCl$_3$): 7.58 (dd, J=0.7, 1.7 Hz, 1H), 7.15 (dd, J=0.7, 3.3 Hz, 1H), 6.56 (dd, J=1.7, 3.3 Hz, 1H), 6.02 (s, 1H), 5.63 (brs, 2H), 3.56 (t, J=5.0 Hz, 4H), 2.60–2.71 (m, 6H), 1.51–1.71 (m, 4H), 1.18 (s, 3H), 0.91 (t, J=7.6 Hz, 3H)

Mass (m/z): 385 (M$^+$)

IR (KBr): 3417, 3139, 2972, 1660, 1606, 1564, 1516, 1479, 1443, 1416, 1338, 1223, 1122, 1020, 770 cm$^{-1}$

Melting point: 196–197° C.

Elemental analysis: as C$_{19}$H$_{27}$N$_7$O$_2$ Calculated (%): C=59.20; H=7.06; N=25.44; Found (%): C=59.29; H=7.06; N=25.05.

EXAMPLE 9

5-Amino-2-(2-furyl)-7-(4-(3-hydroxy-3-phenylbutyl)piperazinyl)[1,2,4]triazolo[1,5-c]pyrimidine (Compound 9)

Yield: 36% (recrystallized from ethyl acetate-2-propanol; white powder)

$^1$H NMR (δ ppm, CDCl$_3$): 7.58 (dd, J=0.7, 1.7 Hz, 1H), 7.48 (d, J=7.6 Hz, 2H), 7.36 (d, J=7.6 Hz, 2H), 7.25 (d, J=6.6 Hz, 1H), 7.15 (dd, J=0.7, 3.3 Hz, 1H), 6.56 (dd, J=1.7, 3.3 Hz, 1H), 6.02 (s, 1H), 5.63 (brs, 2H), 3.51–3.60 (m, 4H), 2.60–2.70 (m, 2H), 2.17–2.46 (m, 4H), 2.02–2.17 (m, 1H), 1.83–1.97 (m, 1H), 1.52(s, 3H)

Mass (m/z): 451 (M$^+$)

IR (KBr): 3444, 3167, 2972, 2833, 2362, 1652, 1616, 1564, 1513, 1421, 1238, 779 cm$^{-1}$

Melting point: 123–124° C.

Elemental analysis: as C$_{23}$H$_{27}$N$_7$O$_2$ 1.0OH$_2$O Calculated (%): C=61.18; H=6.47; N=21.71; Found (%): C=61.20; H=6.39; N=21.77.

EXAMPLE 10

5-Amino-2-(2-furyl)-7-(4-(3-ethyl-3-hydroxypentyl)piperazinyl)[1,2,4]triazolo[1,5-c]pyrimidine (Compound 10)

Yield: 42% (recrystallized from ethanol-ethyl acetate; pale yellow powder)

$^1$H NMR (δ ppm, CDCl$_3$): 7.58 (dd, J=0.7, 1.7 Hz, 1H), 7.16 (dd, J 0.7, 3.3 Hz, 1H), 6.55 (dd, J=1.7, 3.3 Hz, 1H), 6.02 (s, 1H), 5.65 (brs, 2H), 3.55 (t, J=5.0 Hz, 4H), 2.59–2.65 (m, 6H), 1.40–1.69 (m, 6H), 0.87 (t, J=7.6 Hz, 6H)

Mass (m/z): 399 (M$^+$)

IR (KBr): 3278, 2968, 2833, 2808, 2361, 1659, 1651, 1605, 1441, 1417, 1336, 1236, 1201 cm$^{-1}$

Melting point: 183° C.

Elemental analysis: as C$_{20}$H$_{29}$N$_7$O$_2$ Calculated (%): C=60.13; H=7.32; N=24.54; Found (%): C=60.17; H=7.49; N=24.63.

EXAMPLE 11

5-Amino-2-(2-furyl)-7-(4-(3-methoxy-3-methylbutyl)piperazinyl)[1,2,4]triazolo[1,5-c]pyrimidine (Compound 11)

Yield: 53% (recrystallized from ethyl acetate; white powder)

$^1$H NMR (δ ppm, CDCl$_3$): 7.58 (dd, J=0.7, 1.7 Hz, 1H), 7.15 (dd, J=0.7, 3.3 Hz, 1H), 6.55 (dd, J=1.7, 3.3 Hz, 1H), 6.02 (s, 1H), 5.77 (brs, 2H), 3.56 (t, J=5.0 Hz, 4H), 3.20 (s, 3H), 2.54 (t, J=5.0 Hz, 4H), 2.44 (t, J=8.3 Hz, 2H), 1.72 (t, J=8.3 Hz, 2H), 1.18 (s, 6H)

Mass (m/z): 385 (M$^+$)

IR (KBr): 2972, 2808, 2364, 1668, 1606, 1562, 1513, 1442, 1417, 1377, 1335, 1225, 1126, 1080, 1005, 773 cm$^{-1}$

Melting point: 194–195° C.

Elemental analysis: as C$_{19}$H$_{27}$N$_7$O$_2$ Calculated (%): C=59.20; H=7.06; N=25.43; Found (%): C=59.02; H=7.06; N=25.10.

EXAMPLE 12

5-Amino-2-(2-furyl)-7-(4-(2-hydroxy-1,1-dimethylethyl)piperazinyl)[1,2,4]triazolo[1,5-c]pyrimidine (Compound 12)

Yield: 48% (recrystallized from toluene-hexane; white needles)

$^1$H NMR (δ ppm, CDCl$_3$): 7.59 (dd, J=0.7, 1.7 Hz, 1H), 7.16 (dd, J 0.7, 3.3 Hz, 1H), 6.56 (dd, J=1.7, 3.3 Hz, 1H), 6.03 (s, 1H), 5.62 (brs, 2H), 3.58 (brt, 4H), 3.42 (s, 2H), 2.71 (brt, 4H), 2.36 (s, 1H), 1.09 (s, 6H)

Mass (m/z): 357 (M$^+$)

IR (KBr): 3444, 3167, 2972, 2833, 2362, 1663, 1616, 1560, 1514, 1444, 1230, 978, 771 cm$^{-1}$

Melting point: 213–215° C.

Elemental analysis: as $C_{27}H_{23}N_7O_2$ 0.4$H_2O$ 0.3toluene Calculated (%): C=58.48; H=6.73; N=25.00; Found (%): C=58.31; H=6.65; N=25.05.

EXAMPLE 13

5-Amino-2-(2-furyl)-7-(4-(4-hydroxy-4-methylpentyl)piperazinyl)[1,2,4]triazolo[1,5-c]pyrimidine (Compound 13)

Yield: 68% (recrystallized from ethyl acetate; white powder)

$^1$H NMR (δ ppm, CDCl$_3$): 7.58 (dd, J=0.7, 1.7 Hz, 1H), 7.16 (dd, J=0.7, 3.3 Hz, 1H), 6.55 (dd, J=1.7, 3.3 Hz, 1H), 6.01 (s, 1H), 5.78 (brs, 2H), 3.57 (t, J=5.0 Hz, 4H), 2.59 (t, J=5.0 Hz, 4H), 2.45 (t, J=5.3 Hz, 2H), 1.58–1.74 (m, 4H), 1.22 (s, 6H)

Mass (m/z): 385 (M$^+$)

IR (KBr): 3417, 3153, 2958, 2819, 2364, 1647, 1610, 1560, 1514, 1444, 1417, 1381, 1335, 1236, 1126, 984, 770 cm$^{-1}$

Melting point: 178° C.

Elemental analysis: as $C_{19}H_{27}N_2$ 0.5$H_2O$ Calculated (%): C=57.13; H=6.49; N=27.43; Found (%): C=57.28; H=6.58; N=27.48.

EXAMPLE 14

5-Amino-2-(2-furyl)-7-(4-(5-hydroxy-5-methylhexyl)piperazinyl)[1,2,4]triazolo[1,5-c]pyrimidine (Compound 14)

Yield: 49% (recrystallized from ethyl acetate; white powder)

$^1$H NMR (δ ppm, CDCl$_3$): 7.58 (dd, J=0.7, 1.7 Hz, 1H), 7.16 (dd, J=0.7, 3.3 Hz, 1H), 6.55 (dd, J=1.7, 3.3 Hz, 1H), 6.01 (s, 1H), 5.90 (brs, 2H), 3.55 (t, J=5.0 Hz, 4H), 2.51 (t, J=5.0 Hz, 4H), 2.39 (t, J=7.6 Hz, 2H), 1.26–1.56 (m, 6H), 1.22 (s, 6H)

Mass (m/z): 399 (M$^+$)

IR (KBr): 3417, 3389, 3278, 3167, 2958, 2847, 2359, 1662, 1614, 1564, 1513, 1444, 1417, 1378, 1336, 1234, 773 cm$^{-1}$

Melting point: 148° C.

Elemental analysis: as $C_{20}H_{29}N_7O_2$ 1.2$H_2O$ Calculated (%): C=57.04; H=7.51; N=23.28; Found (%): C=57.07; H=7.55; N=23.21.

EXAMPLE 15

5-Amino-2-(2-furyl)-7-(4-(imidazo[1,2-a]pyridin-2-ylmethyl)piperazinyl)[1,2,4]triazolo[1,5-c]pyrimidine (Compound 15)

In 7.5 mL of DMF, 500 mg (1.75 mmol) of Compound F and 582 mg (3.51 mmol) of imidazo[1,2-a]pyridin-2-ylmethyl chloride were dissolved. The solution was cooled to 0° C. in an ice bath, and then 1.6 mL of triethylamine was added thereto, followed by stirring at room temperature overnight. After completion of the reaction, water was added to the reaction mixture and a 1.0 mol/L sodium hydroxide solution was further added thereto to adjust the solution to be basic. Then, the mixture was extracted by adding chloroform, and the organic layer was washed with water and brine, and then dried over anhydrous magnesium sulfate. After evaporation of the solvent, the resulting residue was purified by silica gel column chromatography (2% methanol-chloroform) and then recrystallized from ethanol to obtain 374 mg of Compound 15 as white powder (yield: 51%).

$^1$H NMR (δ ppm, CDCl$_3$): 8.07 (d, J=6.9 Hz, 1H), 7.59 (s, 1H), 7.58–7.54 (m, 2H), 7.18–7.12 (m, 2H), 6.76 (dd, J=6.1, 7.4 Hz, 1H), 6.54 (dd, J=1.7, 3.3 Hz, 1H), 6.01 (s, 1H), 5.65 (brs, 2H), 3.77 (s, 2H), 3.59 (t, J=5.0 Hz, 4H), 2.67 (t, J=5.0 Hz, 4H)

Mass (m/z): 415 (M$^+$)

IR (KBr): 1666, 1651, 1606, 1446, 1216, 742 cm$^{-1}$

Melting point: 220–221° C.

Elemental analysis: as $C_{21}H_{21}N_9O$ Calculated (%): C=60.71; H=5.09; N=30.34; Found (%): C=60.70; H=5.15; N=30.25.

Compounds 16 to 18 were obtained by carrying out Examples 16 to 18 in a manner similar to that in Example 15.

EXAMPLE 16

5-Amino-2-(2-furyl)-7-(4-(imidazo[1,2-a]pyrazin-2-ylmethyl)piperazinyl)[1,2,4]triazolo[1,5-c]pyrimidine (Compound 16)

Yield: 53% (recrystallized from ethanol; white powder)

$^1$H NMR (δ ppm, CDCl$_3$): 9.06 (s, 1H), 8.04 (dd, J=1.6, 4.6 Hz, 1H), 7.88 (d, J=4.6 Hz, 1H), 7.69 (s, 1H), 7.55 (dd, J=0.7, 1.7 Hz, 1H), 7.14 (dd, J=0.7, 3.3 Hz, 1H), 6.55 (dd, J=1.7, 3.3 Hz, 1H), 6.02 (s, 1H), 5.65 (brs, 2H), 3.84 (s, 2H), 3.62 (t, J=5.0 Hz, 4H), 2.68 (t, J=5.0 Hz, 4H)

Mass (m/z): 416 (M$^+$)

IR (KBr): 1666, 1606, 1234, 1213, 773 cm$^{-1}$

Melting point: 242–244° C.

Elemental analysis: as $C_{20}H_{20}N_{10}O$ 1.1$H_2O$ Calculated (%): C=55.06; H=5.13; N=32.11; Found (%): C=55.22; H=5.13; N=31.91.

EXAMPLE 17

5-Amino-2-(2-furyl)-7-(4-(imidazo[1,2-a]pyrimidin-2-ylmethyl)piperazinyl)[1,2,4]triazolo[1,5-c]pyrimidine (Compound 17)

Yield: 16% (recrystallized from ethanol; pale brown powder)

$^1$H NMR (δ ppm, DMSO-d$_6$): 8.92 (dd, J=2.0, 6.6 Hz, 1H), 8.49 (dd, J=2.2, 4.1 Hz, 1H), 7.86 (d, J=0.8 Hz, 1H), 7.83 (s, 1H), 7.61 (brs, 2H), 7.07–7.01 (m, 2H), 6.66 (dd, J=0.7, 2.6 Hz, 1H), 6.02 (s, 1H), 3.70 (s, 2H), 3.54 (t, J=7.0 Hz, 4H), 2.58 (t, J=7.0 Hz, 4H)

Mass (m/z): 416 (M$^+$)

IR (KBr): 1647, 1608, 1562, 1512, 1437, 1232, 773 cm$^{-1}$

Melting point: 244–246° C.

Elemental analysis: as $C_{20}H_{20}N_{10}O$ 1.2$H_2O$ Calculated (%): C=54.84; H=5.15; N=31.97; Found (%): C=54.72; H=4.87; N=31.94.

EXAMPLE 18

5-Amino-7-(4-(benzimidazol-2-ylmethyl)piperazinyl)-2-(2-furyl)[1,2,4]triazolo[1,5-c]pyrimidine (Compound 18)

Yield: 31% (recrystallized from ethanol; pale brown powder)

¹H NMR (δ ppm, CDCl₃): 7.58 (dd, J=0.7, 1.7 Hz, 1H), 7.30–7.23 (m, 4H), 7.15 (dd, J=0.7, 3.3 Hz, 1H), 6.56 (dd, J=1.7, 3.3 Hz, 1H), 6.03 (s, 1H), 5.63 (brs, 2H), 3.90 (s, 2H), 3.60 (t, J=5.0 Hz, 4H), 2.68 (t, J=5.0 Hz, 4H)

Mass (m/z): 415 (M⁺)

IR (KBr): 1658, 1606, 1564, 1444, 1224, 999, 748 cm⁻¹

Melting point: 284–286° C.

Elemental analysis: as $C_{21}H_{21}N_9O$ Calculated (%): C=60.71; H=5.09; N=30.34; Found (%): C=60.52; H=5.34; N=30.07.

EXAMPLE 19

5-Amino-7-(4-(benzothiazol-2-ylmethyl) piperazinyl)-2-(2-furyl)[1,2,4]triazolo[1,5-c] pyrimidine (Compound 19)

Compound 19 was obtained using a corresponding bromide, instead of the chloride, in a manner similar to that in Example 15.

Yield: 19% (recrystallized from ethanol; pale brown powder)

¹H NMR (δ ppm, CDCl₃): 8.00 (d, J=7.2 Hz, 1H), 7.88 (d, J=7.2 Hz, 1H), 7.59 (dd, J=0.7, 1.7 Hz, 1H), 7.45 (dt, J=1.3, 8.2 Hz, 1H), 7.39 (dd, J=1.3, 8.2 Hz, 1H), 7.16 (dd, J=0.7, 3.3 Hz, 1H), 6.56 (dd, J=1.7, 3.3 Hz, 1H), 6.04 (s, 1H), 5.60 (brs, 2H), 4.02 (s, 2H), 3.63 (t, J=5.0 Hz, 4H), 2.75 (t, J=5.0 Hz, 4H)

Mass (m/z): 432 (M⁺)

IR (KBr): 1652, 1612, 1560, 1440, 1236, 1203 cm⁻¹

Melting point: 218–219° C.

Elemental analysis: as $C_{21}H_{20}N_8OS$ Calculated (%): C=58.32; H=4.66; N=25.91; Found (%): C=58.10; H=4.99; N=26.15.

EXAMPLE 20

5-Amino-7-(4-(benzo-2,1,3-thiadiazol-5-ylmethyl) piperazinyl)-2-(2-furyl)[1,2,4]triazolo[1,5-c] pyrimidine (Compound 20)

Compound 20 was obtained using a corresponding methanesulfonate, instead of the chloride, in a manner similar to that in Example 15.

Yield: 70% (recrystallized from ethanol; white powder)

¹H NMR (δ ppm, CDCl₃): 7.99 (s, 1H), 7.94 (d, J=7.6 Hz, 1H), 7.59 (dd, J=1.6, 7.6 Hz, 1H), 7.58 (dd, J=0.7, 1.7 Hz, 1H), 7.15 (dd, J=0.7, 3.3 Hz, 1H), 6.56 (dd, J=1.7, 3.3 Hz, 1H), 6.03 (s, 1H), 5.64 (brs, 2H), 3.72 (s, 2H), 3.58 (t, J=5.0 Hz, 4H), 2.60 (t, J=5.0 Hz, 4H)

Mass (m/z): 433 (M⁺)

IR (KBr): 1660, 1606, 1444, 1222, 758 cm⁻¹

Melting point: 210–211° C.

Elemental analysis: as $C_{20}H_{19}N_9OS$ Calculated (%): C=55.41; H=4.42; N=29.08; Found (%): C=55.38; H=4.47; N=28.99.

EXAMPLE 21

5-Amino-2-(2-furyl)-7-(4-(5-methylisoxazol-3-ylmethyl)piperazinyl)[1,2,4]triazolo[1,5-c] pyrimidine (Compound 21)

Into 15 mL of dichloromethane, 1.50 g (5.26 mmol) of Compound F and 934 mg (8.42 mmol) of 5-methylisoxazole-3-carboxaldehyde were dissolved, and the solution was cooled to 0° C. in an ice bath. Then, 1.5 mL of acetic acid and 1.78 g (8.42 mmol; 1.6 eq.) of sodium triacetoxyborohydride were added thereto, followed by stirring at room temperature overnight. After completion of the reaction, water was added to the reaction mixture, and a 1.0 mol/L aqueous sodium hydroxide solution was further added thereto to adjust the solution to be basic. Then, the mixture was extracted by adding chloroform, and the organic layer was washed with water and brine, and then dried over anhydrous magnesium sulfate. After evaporation of the solvent, the resulting residue was purified by silica gel column chromatography (2% methanol-chloroform) and then recrystallized from ethanol to obtain 222 mg of Compound 21 as white powder (yield: 11%).

¹H NMR (δ ppm, CDCl₃): 7.58 (dd, J=0.7, 1.7 Hz, 1H), 7.15 (dd, J=0.7, 3.3 Hz, 1H), 6.55 (dd, J=1.7, 3.3 Hz, 1H), 6.03 (s, 1H), 6.02 (s, 1H), 5.60 (brs, 2H), 3.61 (s, 2H), 3.56 (t, J=5.0 Hz, 4H), 2.56 (t, J=5.0 Hz, 4H), 2.42 (s, 3H)

Mass (m/z): 380 (M⁺)

IR (KBr): 1654, 1614, 1564, 1209 cm⁻¹

Melting point: 222–224° C.

Elemental analysis: as $C_{18}H_{20}N_8O_2$ Calculated (%): C=56.83; H=5.30; N=29.46; Found (%): C=56.80; H=5.45; N=29.12.

EXAMPLE 22

5-Amino-2-(2-furyl)-7-(3-methyl-4-(5-methylisoxazol-3-ylmethyl)piperazinyl)[1,2,4] triazolo[1,5-c]pyrimidine (Compound 22)

Compound 22 was obtained in a manner similar to that in Example 15.

Yield: 40% (recrystallized from ethanol; white powder)

¹H NMR(δ ppm, CDCl₃): 7.58 (dd, J=0.7, 1.7 Hz, 1H), 7.15 (dd, J=0.7, 3.3 Hz, 1H), 6.55 (dd, J=1.7, 3.3 Hz, 1H), 5.99 (s, 1H), 5.98 (s, 1H), 5.70 (brs, 2H), 3.98 (s, 1H), 3.92 (s, 1H), 3.89 (d, J=14.2 Hz, 1H), 3.62 (d, J=14.2 Hz, 1H), 3.13 (dt, J=3.3, 10.6 Hz, 1H), 2.89–2.82 (m, 3H), 2.57–2.43 (m, 1H), 2.41 (d, J=6.5 Hz, 3H), 1.20 (d, J=6.3 Hz, 3H)

Mass (m/z): 394 (M⁺)

IR (KBr): 1652, 1648, 1606, 1238 cm⁻¹

Melting point: 183–185° C.

Elemental analysis: as $C_{19}H_{22}N_8O_2$ 2.0 HCl 2.1 H₂O Calculated (%): C=45.17; H=5.63; N=22.18; Found (%): C=45.17; H=5.47; N=22.07.

Compounds 23 to 25 were obtained by carrying out Examples 23 to 25 using corresponding methanesulfonates, instead of the chloride, in a manner similar to that in Example 15.

EXAMPLE 23

5-Amino-2-(2-furyl)-7-(4-(1-(5-methylisoxazol-3-yl) ethyl)piperazinyl)[1,2,4]triazolo[1,5-c]pyrimidine (Compound 23)

Yield: 31% (recrystallized from ethanol; pale brown powder)

¹H NMR (δ ppm, CDCl₃): 7.58 (dd, J=0.7, 1.7 Hz, 1H), 7.15 (dd, J=0.7, 3.3 Hz, 1H), 6.55 (dd, J=1.7, 3.3 Hz, 1H), 6.00 (s, 1H), 5.96 (s, 1H), 5.73 (brs, 2H), 3.80 (q, J=6.9 Hz, 1H), 3.54 (t, J=5.0 Hz, 4H), 2.58 (t, J=5.0 Hz, 4H), 2.41 (s, 3H), 1.43 (d, J=6.9 Hz, 3H)

Mass (m/z): 394 (M$^+$)
IR (KBr): 1666, 1604, 1444, 1227, 767 cm$^{-1}$
Melting point: 106–108° C.

EXAMPLE 24

5-Amino-2-(2-furyl)-7-(4-(3-methylisoxazol-4-ylmethyl)piperazinyl)[1,2,4]triazolo[1,5-c]pyrimidine (Compound 24)

Yield: 56% (recrystallized from ethanol; white powder)
$^1$H NMR (δ ppm, CDCl$_3$): 8.23 (s, 1H), 7.59 (dd, J=0.7, 1.7 Hz, 1H), 7.15 (dd, J=0.7, 3.3 Hz, 1H), 6.56 (dd, J=1.7, 3.3 Hz, 1H), 6. 02 (s, 1H), 5.62 (brs, 2H), 3.54 (t, J=5.0 Hz, 4H), 3.38 (s, 2H), 2.51 (t, J=5.0 Hz, 4H), 2.33 (s, 3H)
Mass (m/z): 380 (M$^+$)
IR (Kbr): 1666, 1648, 1604, 1446, 1333, 1207, 999 cm$^{-1}$
Melting point: 233–234° C.
Elemental analysis: as C$_{18}$H$_{20}$N$_8$O$_2$ 0.2H$_2$O Calculated (%): C=56.30; H=5.35; N=29.18; Found (%): C=56.08; H=5.37; N=29.41.

EXAMPLE 25

5-Amino-2-(2-furyl)-7-(4-(5-methyl-3-phenylisoxazol-4-ylmethyl)piperazinyl)[1,2,4]triazolo[1,5-c]pyrimidine (Compound 25)

Yield: 82% (recrystallized from ethanol; white powder)
$^1$H NMR (δ ppm, CDCl$_3$): 7.97–7.93 (m, 2H), 7.59 (dd, J 0.7, 1.7 Hz, 1H), 7.47–7.44 (m, 3H), 7.16 (dd, J=0.7, 3.3 Hz, 1H), 6.56 (dd, J=1.7, 3.3 Hz, 1H), 6.03 (s, 1H), 5.66 (brs, 2H), 3.56 (t, J=5.0 Hz, 4H), 3.34 (s, 2H), 2.54 (t, J=5.0 Hz, 4H), 2.47 (s, 3H)
Mass (m/z): 456 (M$^+$)
IR (KBr): 1653, 1604, 1560, 1444, 1234 cm$^{-1}$
Melting point: 244–246° C.
Elemental analysis: as C$_{24}$H$_{24}$N$_8$O$_2$ Calculated (%): C=63.15; H=5.30; N=24.55; Found (%): C=63.26; H=5.46; N=24.74.

Compounds 26 and 27 were obtained by carrying out the following Examples 26 and 27 using corresponding aldehydes in a manner similar to that in Example 21.

EXAMPLE 26

5-Amino-2-(2-furyl)-7-(4-(3-oxo-3,4-dihydro-2H-benzo[1,4]oxazin-7-ylmethyl)piperazinyl)[1,2,4]triazolo[1,5-c]pyrimidine (Compound 26)

Yield: 15% (recrystallized from ethanol; white powder)
$^1$H NMR (δ ppm, CDCl$_3$): 8.04 (brs, 1H), 7.58 (dd, J=0.7, 1.7 Hz, 1H), 7.15 (dd, J=0.7, 3.3 Hz, 1H), 7.00 (s, 1H), 6.93 (d, J=7.9 Hz, 1H), 6.74 (d, J=7.9 Hz, 1H), 6.55 (dd, J=1.7, 3.3 Hz, 1H), 6.01 (s, 1H), 5.62 (brs, 2H), 4.62 (s, 2H), 3.54 (t, J=5.0 Hz, 4H), 3.47 (s, 2H), 2.53 (t, J=5.0 Hz, 4H)
Mass (m/z): 446 (M$^+$)
IR (KBr): 1606, 1230, 773, 505, 487 cm$^{-1}$
Melting point: 287–288° C.
Elemental analysis: as C$_{22}$H$_{22}$N$_8$O$_3$ Calculated (%): C=59.19; H=4.97; N=25.10; Found (%): C=59.23; H=5.06; N=24.71.

EXAMPLE 27

5-Amino-2-(2-furyl)-7-(4-(3-oxo-3,4-dihydro-2H-benzo[1,4]oxazin-6-ylmethyl)piperazinyl)[1,2,4]triazolo[1,5-c]pyrimidine (Compound 27)

Yield: 50% (recrystallized from ethanol; pale brown powder)
$^1$H NMR (δ ppm, DMSO-d$_6$): 10.67 (brs, 1H), 7.87 (t, J=0.8 Hz, 1H), 7.61 (brs, 2H), 7.06 (d, J=3.6 Hz, 1H), 6.90–6.87(m, 3H), 6.67 (dd, J=0.7, 2.6 Hz, 1H), 6.01 (s, 1H), 4.55 (s, 2H), 3.51 (t, J=7.0 Hz, 4H), 3.41 (s, 2H), 2.42 (t, J=7.0 Hz, 4H)
Mass (m/z): 446 (M$^+$)
IR (KBr): 1677, 1645, 1606, 1564, 1197, 773 cm$^{-1}$
Melting point: 284–285° C.
Elemental analysis: as C$_{22}$H$_{22}$N$_8$O$_3$ Calculated (%): C=59.19; H=4.97; N=25.10; Found (%): C=59.01; H=5.28; N=25.11.

EXAMPLE 28

5-Amino-2-(2-furyl)-7-(4-(1-methoxycyclopropylmethyl)piperazinyl)[1,2,4]triazolo[1,5-c]pyrimidine (Compound 28)

Compound 28 was obtained using a corresponding piperazine derivative in a manner similar to that in Example 1.
Yield: 59% (recrystallized from ethanol-ethyl acetate; white powder)
$^1$H NMR (δ ppm, CDCl$_3$): 7.58 (dd, J=0.7, 1.7 Hz, 1H), 7.15 (dd, J=0.7, 3.3 Hz, 1H), 6.55 (dd, J 1.7, 3.3 Hz, 1H), 6.02 (s, 1H), 5.83 (brs, 2H), 3.58 (t, J=5.0 Hz, 4H), 3.34 (s, 3H), 2.65 (t, J=5.0 Hz, 4H), 2.55 (s, 2H), 0.83 (dd, J=5.0, 6.6 Hz, 2H), 0.48 (dd, J=5.0, 6.6 Hz, 2H)
Mass (m/z): 370 (M+1)
IR (KBr): 3458, 3115, 2835, 1655, 1608, 1556, 1514, 1470, 1443, 1417, 1331, 1230, 1205, 1117, 1063, 1012, 984, 906, 885, 771 cm$^{-1}$
Melting point: 201–202° C.
Elemental analysis: as C$_{18}$H$_{23}$N$_7$O$_2$ 0.3H$_2$O Calculated (%): C=57.68; H=6.34; N=26.16; Found (%): C=55.61; H=6.24; N=26.09.

Formulation Example 1

Tablets

Tablets having the following composition are prepared in the usual way.

| | |
|---|---|
| Compound 1 | 10 mg |
| Lactose | 30 mg |
| Potato starch | 15 mg |
| Polyvinyl alcohol | 1.5 mg |
| Magnesium stearate | 0.5 mg |

Formulation Example 2

Capsules

Capsules having the following composition are prepared in the usual way.

| | |
|---|---|
| Compound 2 | 10 mg |
| Lactose | 100 mg |
| Magnesium stearate | 2.5 mg |

These components are mixed and packed in gelatin capsules.

Formulation Example 3

Injections

Injections having the following composition are prepared in the usual way.

| | |
|---|---|
| Compound 15 | 2 mg |
| Purified soybean oil | 200 mg |
| Purified egg yolk lecithin | 24 mg |
| Glycerol for injection | 50 mg |
| Distilled water for injection | 1.72 ml |

INDUSTRIAL APPLICABILITY

The present invention provides novel triazolopyrimidine derivatives or pharmaceutically acceptable salts thereof, which have adenosine $A_{2A}$ receptor antagonism and are useful for treating or preventing various diseases induced by hyperactivity of an adenosine $A_{2A}$ receptor (for example, parkinson's disease, senile dementia or depression).

What is claimed is:

1. A [1,2,4]triazolo[1,5-c]pyrimidine compound represented by formula (I):

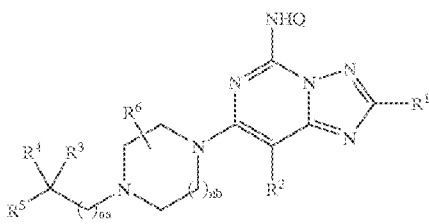

wherein
- $R^1$ represents substituted or unsubstituted aryl, or a substituted or unsubstituted aromatic heterocyclic group;
- $R^2$ represents a hydrogen atom, halogen, substituted or unsubstituted lower alkyl, substituted or unsubstituted aryl, or a substituted or unsubstituted aromatic heterocyclic group;
- na and nb independently represent an integer of 0 to 4;
- Q represents a hydrogen atom or 3,4-dimethoxybenzyl;
- $R^6$ represents a hydrogen atom, substituted or unsubstituted lower alkyl, halogen, or hydroxy;
- $R^3$ represents (I) hydroxy, (ii) hydroxy-lower alkyl, (iii) substituted or unsubstituted lower alkoxy, or (iv) is selected from the group consisting of substituted or unsubstituted imidazo[1,2-a]pyridyl, substituted or unsubstituted imidazo[1,2-a]pyrazinyl, substituted or unsubstituted imidazo[1,2-a]pyrimidinyl, substituted or unsubstituted benzimidazolyl, substituted or unsubstituted benzothiazolyl, substituted or unsubstituted benzo-2,1,3-thiadiazolyl, substituted or unsubstituted isoxazolyl, and substituted or unsubstituted 3-oxo-3,4-dihydro-2H-benzo[1,4]oxazinyl;

or a pharmaceutically acceptable salt thereof,
with the provisos (i) when $R^3$ represents hydroxy, hydroxy-lower alkyl, or substituted or unsubstituted lower alkoxy, then $R^4$ and $R^5$ independently represent substituted or unsubstituted lower alkyl or substituted or unsubstituted aryl, or $R^4$ and $R^5$ form a substituted or unsubstituted saturated carbocycle together with the adjacent carbon atom, and (ii) when $R^3$ is selected from the group consisting of substituted or unsubstituted imidazo[1,2-a]pyridyl, substituted or unsubstituted imidazo[1,2-a]pyrazinyl, substituted or unsubstituted imidazo[1,2-a]pyrimidinyl, substituted or unsubstituted benzimidazolyl, substituted or unsubstituted benzothiazolyl, substituted or unsubstituted benzo-2,1,3-thiadiazolyl, substituted or unsubstituted isoxazolyl, and substituted or unsubstituted 3-oxo-3,4-dihydro-2H-benzo[1,4]oxazinyl, then $R^4$ and $R^5$ independently represent a hydrogen atom, substituted or unsubstituted lower alkyl, or substituted or unsubstituted aryl, or $R^4$ and $R^5$ form a substituted or unsubstituted saturated carbocycle together with the adjacent carbon atom.

2. The [1,2,4]triazolo[1,5-c]pyrimidine compound according to claim 1, wherein $R^3$ is hydroxy, hydroxy-lower alkyl, or substituted or unsubstituted lower alkoxy, or a pharmaceutically acceptable salt thereof.

3. The [1,2,4]triazolo[1,5-c]pyrimidine compound according to claim 1, wherein $R^3$ is selected from the group consisting of substituted or unsubstituted imidazo[1,2-a]pyridyl, substituted or unsubstituted imidazo[1,2-a]pyrazinyl, substituted or unsubstituted imidazo[1,2-a]pyrimidinyl, substituted or unsubstituted benzimidazolyl, substituted or unsubstituted benzothiazolyl, substituted or unsubstituted benzo-2,1,3-thiadiazolyl, substituted or unsubstituted isoxazolyl, and substituted or unsubstituted 3-oxo-3,4-dihydro-2H-benzo[1,4]oxazinyl, or a pharmaceutically acceptable salt thereof.

4. The [1,2,4]triazolo[1,5-c]pyrimidine compound according to any one of claims 1 to 3, wherein Q is a hydrogen atom, or a pharmaceutically acceptable salt thereof.

5. The [1,2,4]triazolo[1,5-c]pyrimidine compound according to claim 4, wherein $R^2$ is a hydrogen atom, or a pharmaceutically acceptable salt thereof.

6. The [1,2,4]triazolo[1,5-c]pyrimidine compound according to claim 5, wherein $R^1$ is a substituted or unsubstituted aromatic heterocyclic group, or a pharmaceutically acceptable salt thereof.

7. The [1,2,4]triazolo[1,5-c]pyrimidine compound according to claim 5, wherein $R^1$ is furyl, or a pharmaceutically acceptable salt thereof.

8. The [1,2,4]triazolo[1,5-c]pyrimidine compound according to claim 7, wherein $R^6$ is a hydrogen atom; na and nb each are 1; $R^3$ is hydroxy; and $R^4$ and $R^5$ each are substituted or unsubstituted lower alkyl; or a pharmaceutically acceptable salt thereof.

9. The [1,2,4]triazolo[1,5-c]pyrimidine compound according to claim 8, wherein $R^4$ and $R^5$ each are methyl, or a pharmaceutically acceptable salt thereof.

10. The [1,2,4]triazolo[1,5-c]pyrimidine compound according to claim 7, wherein $R^6$ is a hydrogen atom; na is 0; nb is 1; $R^3$ is selected from the group consisting of substituted or unsubstituted imidazo[1,2-a]pyridyl, substituted or unsubstituted imidazo[1,2-a]pyrazinyl, substituted or unsubstituted imidazo[1,2-a]pyrimidinyl, substituted or unsubstituted benzimidazolyl, substituted or unsubstituted benzothiazolyl, substituted or unsubstituted benzo-2,1,3-thiadiazolyl, substituted or unsubstituted isoxazolyl, and substituted or unsubstituted 3-oxo-3,4-dihydro-2H-benzo[1,4]oxazinyl; or a pharmaceutically acceptable salt thereof.

11. The [1,2,4]triazolo[1,5-c]pyrimidine compound according to claim 10, wherein $R^3$ is 5-methylisoxazol-3-yl, or a pharmaceutically acceptable salt thereof.

12. A medicament comprising the [1,2,4]triazolo[1,5-c]pyrimidine compound according to any one of claims 1 to 3 or a pharmaceutically acceptable salt thereof, and a pharmaceutically acceptable carrier.

13. A method for inhibiting an adenosine $A_{2A}$ receptor, comprising administering an effective amount of the [1,2,4]triazolo[1,5-c]pyrimidine compound according to claim 4, or a pharmaceutically acceptable salt thereof.

14. A method for inhibiting adenosine $A_{2A}$ receptor, comprising administering an effective amount of the [1,2,4]triazolo[1,5-c]pyrimidine compound according to any one of claims 1 to 3, or a pharmaceutically acceptable salt thereof.

15. The method according to claim 14, wherein the inhibited adenosine $A_{2A}$ receptor is hyperactive.

16. A method for treating depression comprising administering an effective amount of the [1,2,4]triazolo[1,5-c]pyrimidine compound according to any one of claims 1 to 3, or a pharmaceutically acceptable salt thereof.

17. A method for treating Parkinson's disease comprising administering an effective amount of the [1,2,4]triazolo[1,5-c]pyrimidine compound according to any one of claims 1 to 3 or a pharmaceutically acceptable salt thereof.

* * * * *